United States Patent
Sherman et al.

(10) Patent No.: US 7,815,664 B2
(45) Date of Patent: Oct. 19, 2010

(54) SYSTEMS AND METHODS FOR SPINAL STABILIZATION WITH FLEXIBLE ELEMENTS

(75) Inventors: Michael C. Sherman, Memphis, TN (US); Roy Lim, Germantown, TN (US); Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1685 days.

(21) Appl. No.: 11/028,999

(22) Filed: Jan. 4, 2005

(65) Prior Publication Data

US 2006/0149238 A1   Jul. 6, 2006

(51) Int. Cl.
*A61B 17/56* (2006.01)
(52) U.S. Cl. .................. 606/257; 606/250
(58) Field of Classification Search ........... 606/279, 606/246, 264, 265, 60, 250–263; 403/72, 403/102, 103, 108, 109.1, 109.2, 112, 117, 403/139, 179, 345–347
See application file for complete search history.

(56) References Cited

U.S. PATENT DOCUMENTS

| | | | |
|---|---|---|---|
| 1,308,799 A | 7/1919 | Masland | |
| 2,697,433 A | 12/1954 | Zehnder | |
| 4,411,259 A | 10/1983 | Drummond | |
| 4,672,957 A | 6/1987 | Hourahane | |
| 4,733,657 A | 3/1988 | Kluger | |
| 5,180,393 A | 1/1993 | Commarmond | |
| 5,409,488 A * | 4/1995 | Ulrich | 606/260 |
| 5,540,688 A | 7/1996 | Navas | |
| 5,569,248 A | 10/1996 | Mathews | |
| 5,697,977 A | 12/1997 | Pisharodi | |
| 5,702,395 A | 12/1997 | Hopf | |
| 5,704,936 A | 1/1998 | Mazel | |
| 5,720,751 A | 2/1998 | Jackson | |
| 5,910,141 A | 6/1999 | Morrison et al. | |
| 5,961,516 A | 10/1999 | Graf | |
| 6,123,707 A | 9/2000 | Wagner | |
| 6,159,212 A | 12/2000 | Schoedinger, III et al. | |
| 6,162,223 A | 12/2000 | Orsak et al. | |
| 6,235,028 B1 | 5/2001 | Brumfield et al. | |
| 6,267,764 B1 | 7/2001 | Elberg | |
| 6,296,644 B1 * | 10/2001 | Saurat et al. | 606/256 |
| 6,299,616 B1 | 10/2001 | Beger | |
| 6,440,133 B1 | 8/2002 | Beale et al. | |
| 6,530,929 B1 | 3/2003 | Justis et al. | |
| 6,605,088 B1 | 8/2003 | St. Onge et al. | |
| 6,648,888 B1 | 11/2003 | Shluzas | |
| 7,137,985 B2 * | 11/2006 | Jahng | 606/86 A |
| 2002/0072753 A1 | 6/2002 | Cohen | |
| 2002/0161368 A1 * | 10/2002 | Foley et al. | 606/61 |
| 2003/0171749 A1 * | 9/2003 | Le Couedic et al. | 606/61 |

(Continued)

FOREIGN PATENT DOCUMENTS

DE    42 38 339 A1    5/1994

(Continued)

*Primary Examiner*—Eduardo C Robert
*Assistant Examiner*—Tara R Carter

(57) ABSTRACT

Systems and methods are provided for spinal stabilization with flexible elements and other elements engaged to the vertebrae. Also provided are instruments and methods for insertion of the flexible stabilization elements and other elements and for reduction of displacement between adjacent vertebrae in a minimally invasive surgical approach.

28 Claims, 32 Drawing Sheets

U.S. PATENT DOCUMENTS

| | | |
|---|---|---|
| 2003/0191470 A1 | 10/2003 | Ritland |
| 2003/0220643 A1 | 11/2003 | Ferree |
| 2004/0002708 A1* | 1/2004 | Ritland .................. 606/61 |
| 2004/0236328 A1* | 11/2004 | Paul et al. .............. 606/61 |
| 2005/0171540 A1 | 8/2005 | Lim et al. |
| 2006/0142760 A1* | 6/2006 | McDonnell ............. 606/61 |
| 2006/0264942 A1 | 11/2006 | Lim et al. |
| 2008/0091200 A1* | 4/2008 | Kuiper et al. ........... 606/61 |

FOREIGN PATENT DOCUMENTS

| | | |
|---|---|---|
| DE | 100 27 988 A1 | 10/2002 |
| EP | 0 669 109 B1 | 8/1995 |
| EP | 0 677 277 A2 | 10/1995 |
| EP | 0677277 | 10/1995 |
| EP | 1 374 786 A2 | 1/2004 |
| EP | 1574173 | 9/2005 |
| FR | 2799949 | 4/2001 |
| SU | 848009 | 7/1981 |
| WO | WO 93/15666 | 8/1993 |
| WO | WO 01/28436 | 4/2001 |
| WO | WO 01/49192 A1 | 7/2001 |
| WO | WO 02/07622 | 1/2002 |
| WO | WO 03/007829 | 1/2003 |
| WO | WO 2004/096066 | 11/2004 |
| WO | WO 2005/122925 | 12/2005 |

* cited by examiner

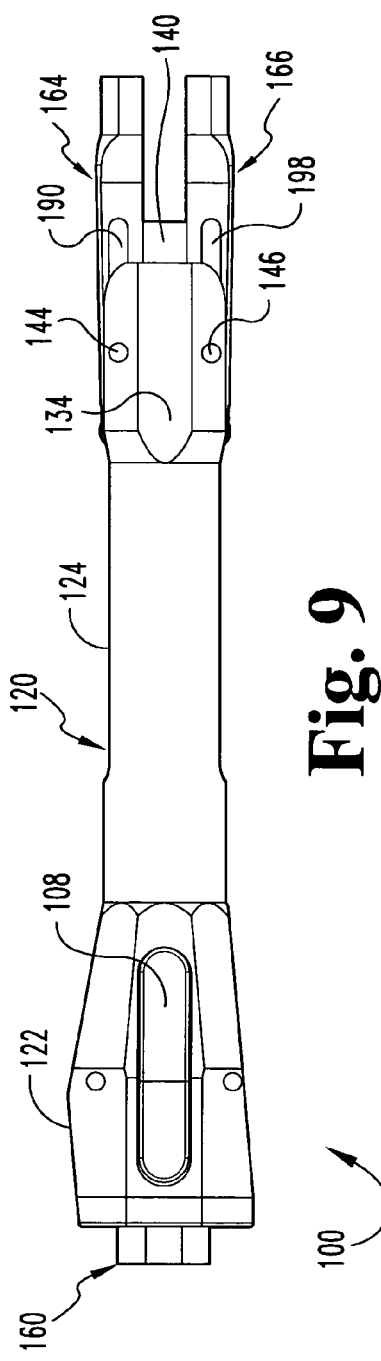
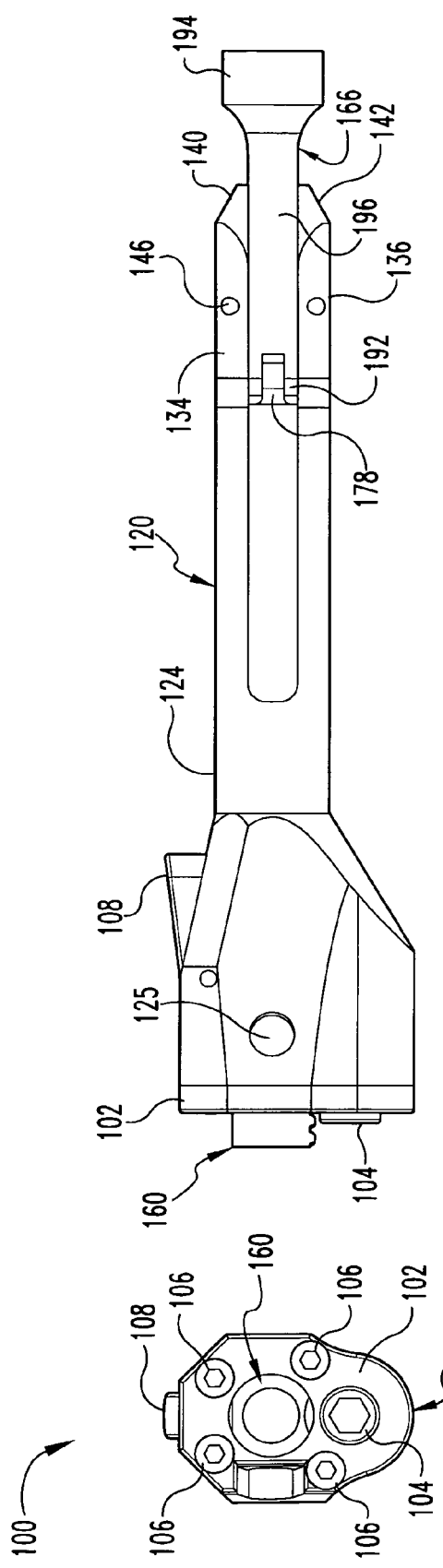
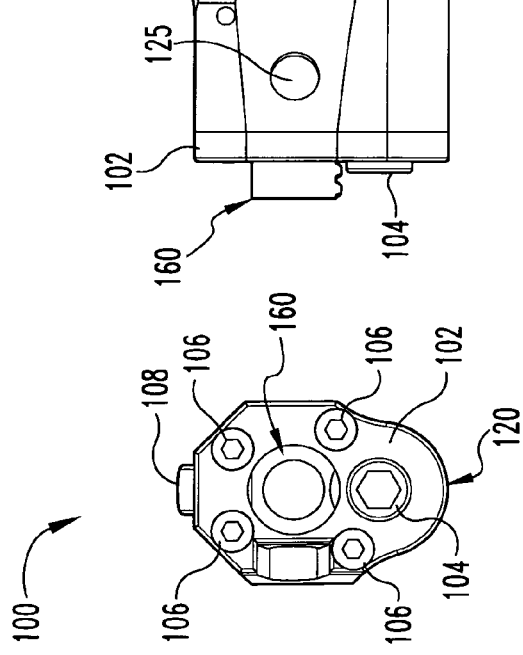

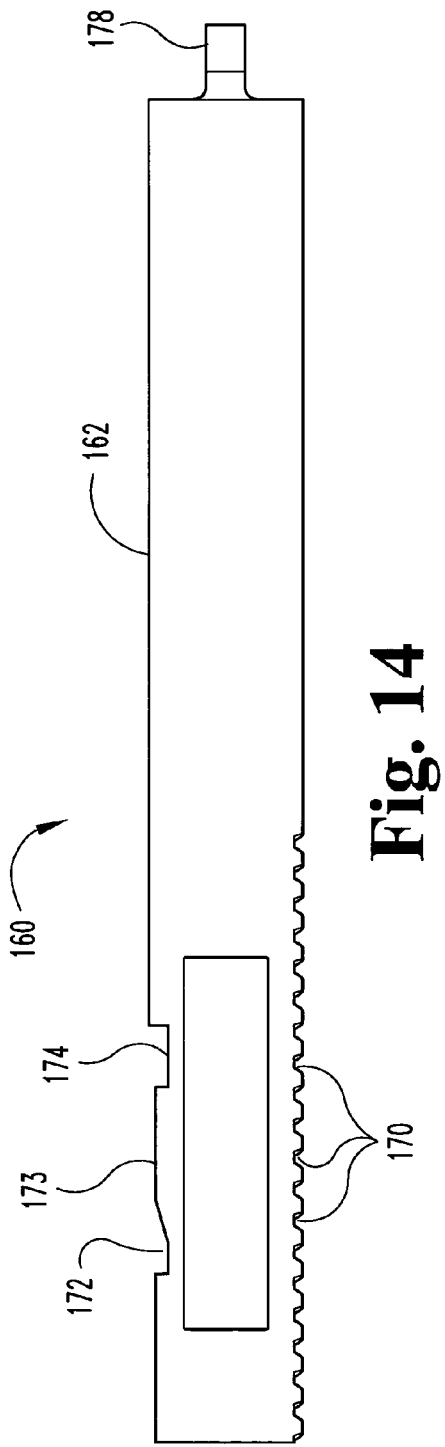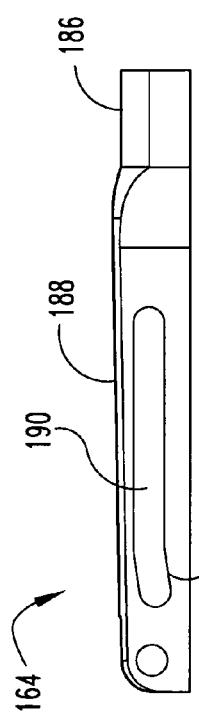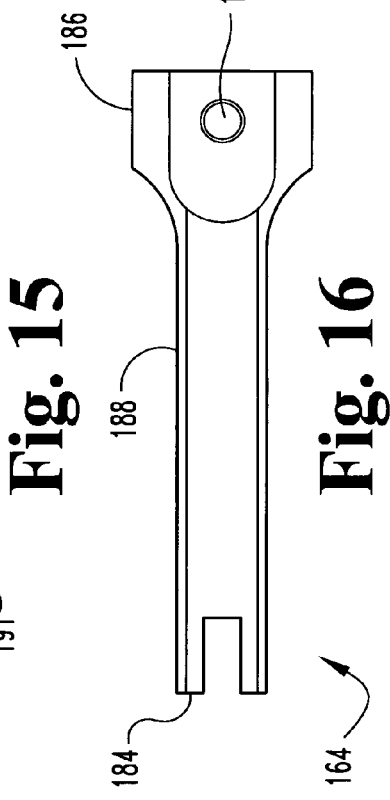

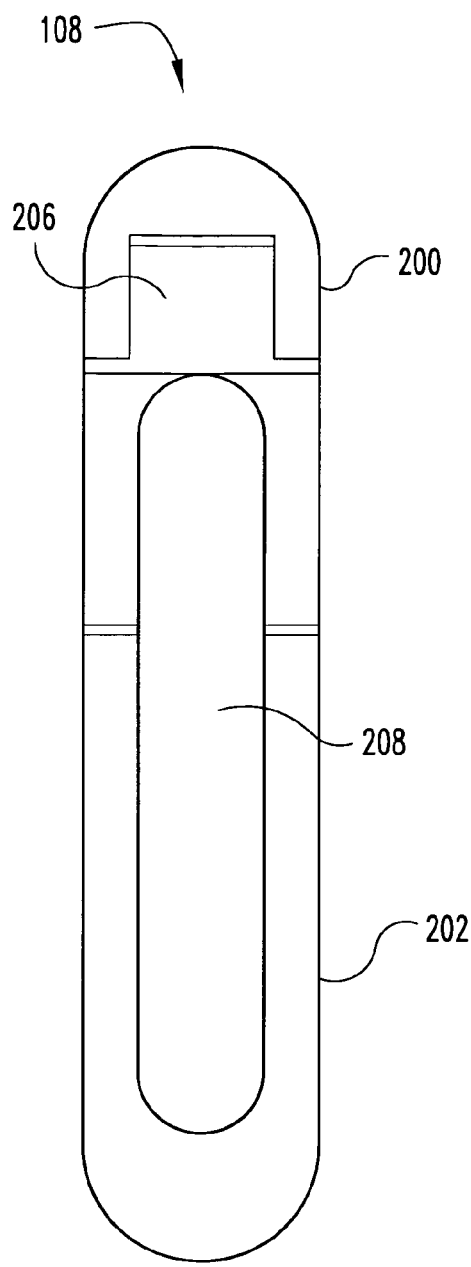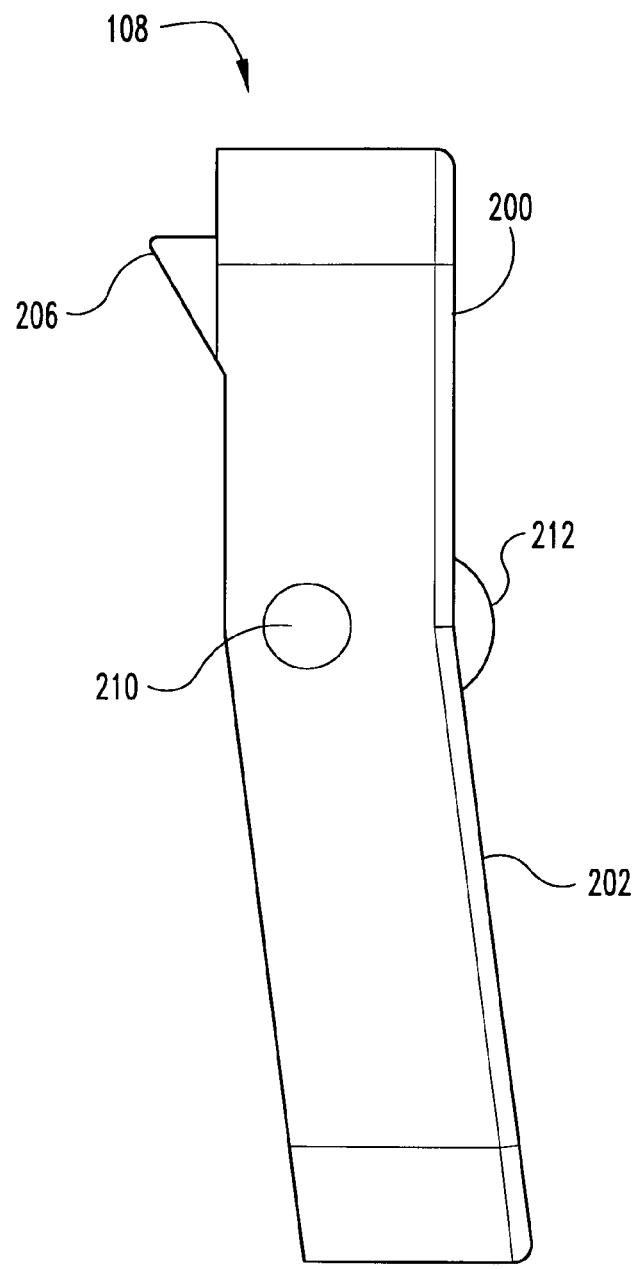
Fig. 17  Fig. 18

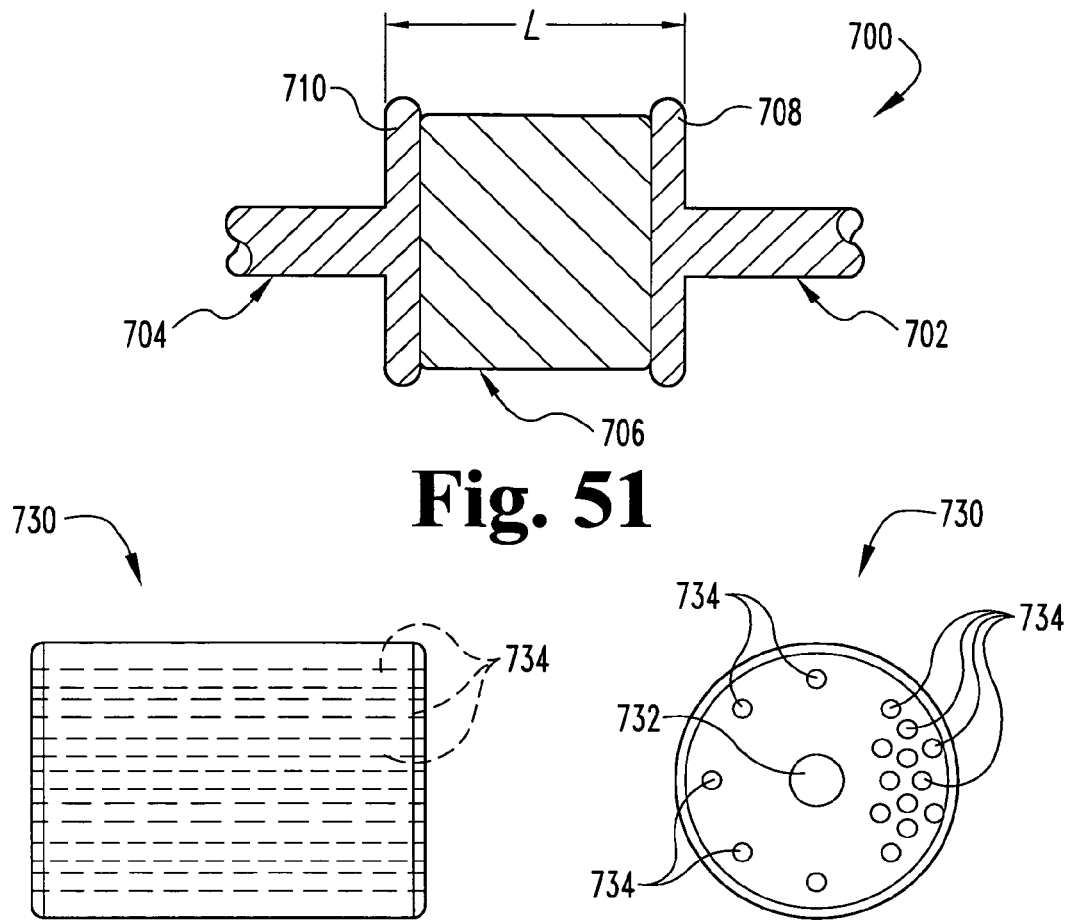
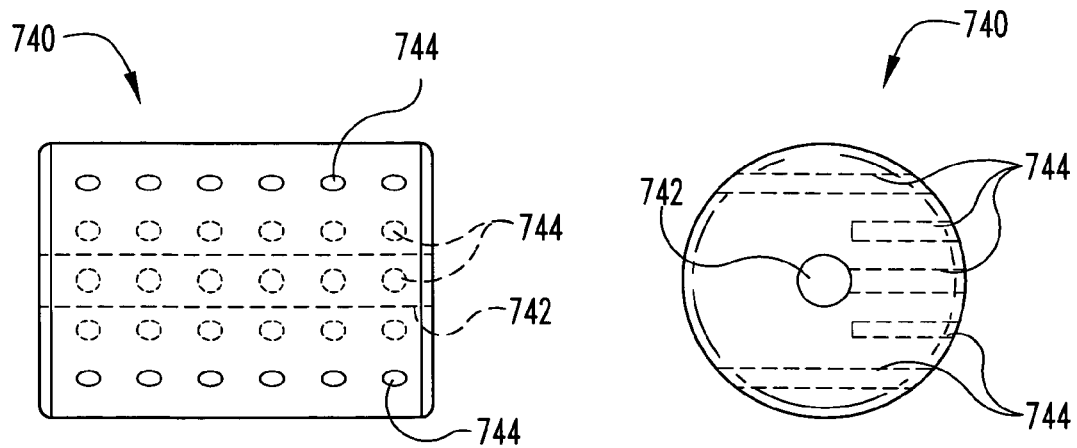

US 7,815,664 B2

SYSTEMS AND METHODS FOR SPINAL STABILIZATION WITH FLEXIBLE ELEMENTS

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure. If one or more of the vertebrae are displaced as a result of spondylolisthesis or other deformity, correction is obtained by pulling the displaced vertebrae into alignment with the adjacent vertebrae prior to securing the rod to the vertebrae.

In these techniques access to the surgical site can be provided by cutting, removing, and/or repositioning skin, tissue and vasculature. This provides the surgeon access to the location where the stabilization device is to be installed, and accommodates placement of instruments to reduce vertebral displacement and to install the stabilization structures. There remains a need for instruments and methods for stabilizing bony structures to provide options for the surgeon in selecting an operative approach for treatment.

SUMMARY

According to one aspect, a system for minimally invasive vertebral reduction and stabilization provided.

According to another aspect, a system for minimally invasive stabilization of a spinal motion segment with motion preservation is provided.

According to another aspect, a system for minimally invasive vertebral reduction and stabilization provided with spinal motion preservation.

Related and additional aspects will be apparent from the following description.

BRIEF DESCRIPTION OF THE DRAWINGS

FIG. 7 is an elevation view of the other anchor extension of the installation instrument of FIG. 1.

FIG. 8 is a left hand end elevation view of the anchor extension of FIG. 7.

FIG. 9 is an elevation view of the anchor extension of FIG. 7 rotated 90 degrees about its longitudinal axis.

FIG. 14 is an elevation view of a proximal portion of the inner member of FIG. 11.

FIG. 15 is an elevation view of a distal portion of the inner member of FIG. 11.

FIG. 16 is an elevation view of the distal portion of the inner member of FIG. 11 rotated 90 degrees about its longitudinal axis from its FIG. 15 orientation.

FIG. 17 is an elevation view of a lock button comprising a portion of the anchor extension of FIG. 7.

FIG. 18 is an elevation view of the lock button of FIG. 17 rotated 90 degrees from its FIG. 17 orientation.

FIG. 51 is a sectional view of a portion of another embodiment connecting element.

FIGS. 52A and 52B are an elevation view and an end view, respectively, of another embodiment flexible intermediate member comprising a portion of a connecting element.

FIGS. 53A and 53B are an elevation view and an end view, respectively, of another embodiment flexible intermediate member comprising a portion of a connecting element.

DESCRIPTION OF THE ILLUSTRATED EMBODIMENTS

Figure 1:
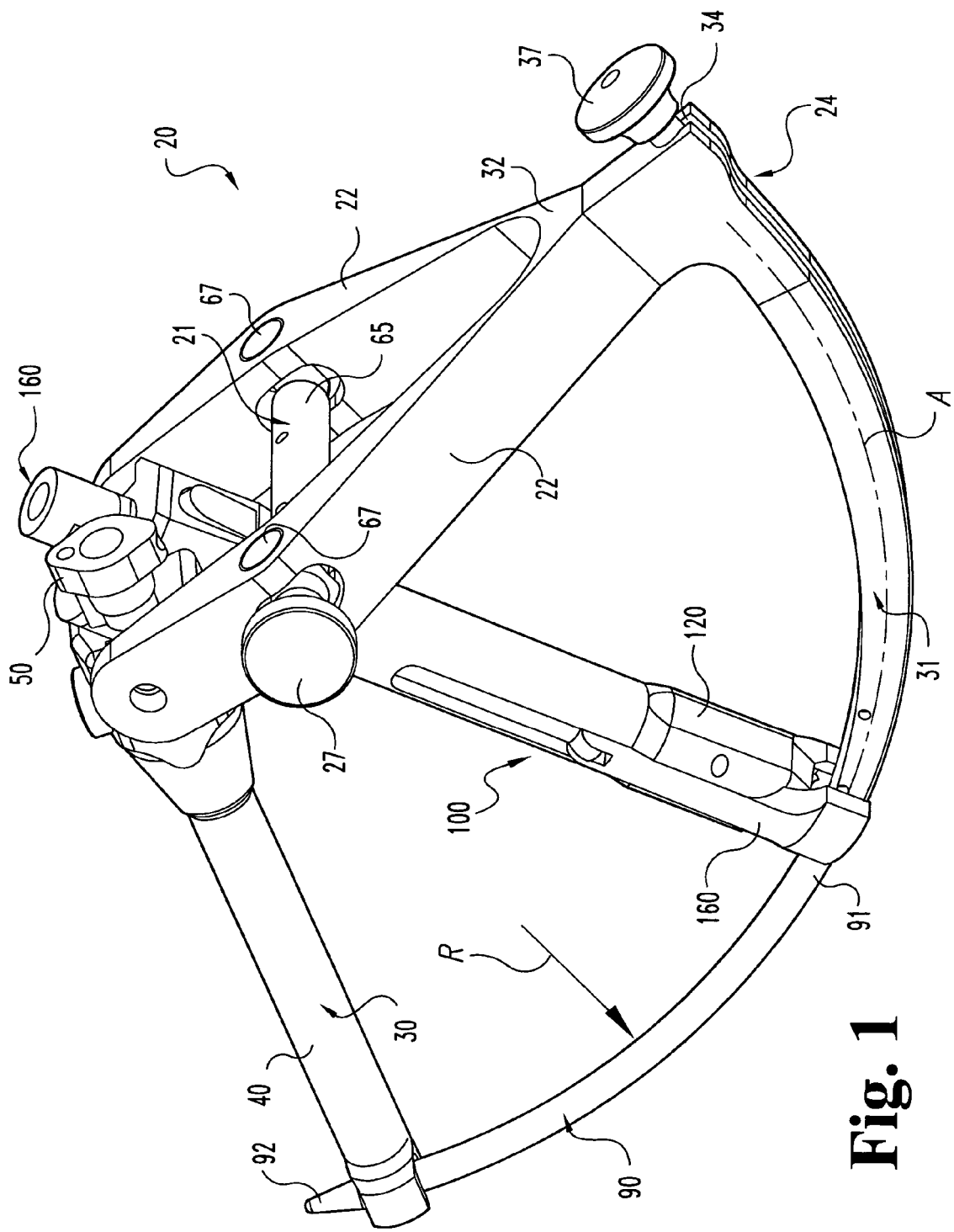
FIG. 1 is a perspective view of a connecting element and an installation instrument for installing the connecting element.
Figure 4:
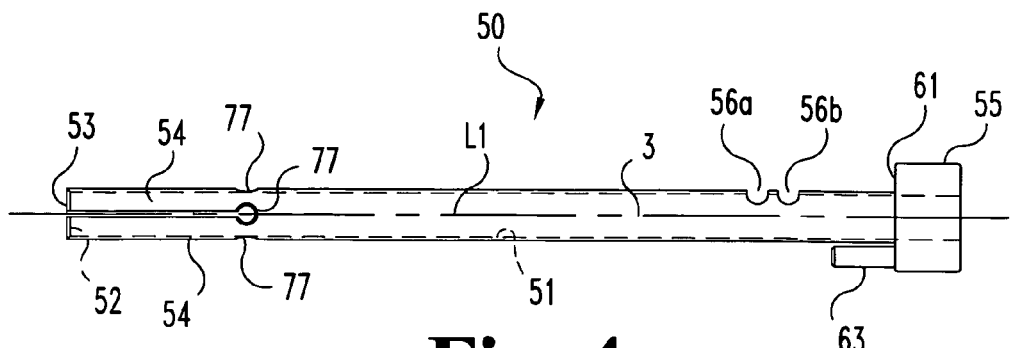
FIG. 4 is an elevation view of an inner sleeve of the anchor extension of FIG. 2.
Figure 5:
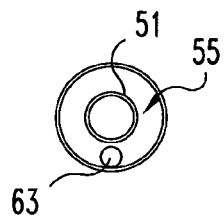
FIG. 5 is an end elevation view of the inner sleeve of FIG. 4.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Instruments and methods for insertion of a connecting element for connection with anchors engaged to bony parts of the body include installation instrument 20 shown in FIG. 1. Installation instrument 20 includes an inserter 24 removably coupled to a connecting element 90. Installation instrument 20 further includes a first anchor extension 30 and a second anchor extension 100 mountable to anchors engaged to bony parts of the body. First anchor extension 30 is mountable to a first anchor, and second anchor extension 100 is mountable to a second anchor. Embodiments where instrument 20 includes only a single anchor and anchor extension, or three or more anchors and anchor extensions, are also contemplated. Inserter 24 is pivotally mounted to anchors extensions 30, 100, and movable relative thereto to guide connecting element 90 from a location remote from the anchors to a location adjacent the anchors for engagement thereto.

In one embodiment, anchor extension 100 includes first and second members movable relative to one another to position the connecting element into a receiver of the anchor. The connecting element is moved along an insertion axis A referenced to at least one of the anchor extensions, and positioned to a location more proximate to the anchors. A second member of anchor extension 100 is mounted to the anchor, and a first member is movable relative to the second member and contactable with the connecting element 90 to move it and the anchor engaged to the second member into a position more proximate one another. The anchor extension 100 moves the connecting element transversely to the insertion axis.

In one form, anchor extension 100 reduces the connecting element into a passageway of the anchor, where the connecting element 90 can be secured to the anchor to stabilize the spinal column segment to which connecting element 90 is engaged. In still a further form, anchor extension 100 is operable to reduce displacement between adjacent vertebrae, such as occurs with spondylolisthesis, and then permit engagement of the connecting element 90 to anchors engaged to the reduced vertebrae to maintain the vertebrae in a more aligned position. Anchor extension 100 provides a further advantage in that reduction and stabilization can be completed in a minimally invasive surgical procedure in which skin and tissue need not be retracted to expose the misaligned vertebrae.

As discussed further below, inserter 24 is configured to releasably engage connecting element 90 and, referenced to anchors in the patient with at least one of the anchor extensions 30, 100, position connecting element 90 in a position adjacent to and extending between the anchors. Anchor extension 100 is configured to contact connecting element 90 and position connecting element 90 and the anchor to which anchor extension 100 is engaged in a position more proximate one another. Anchor extension 30 need not be configured like anchor extension 100 in the illustrated embodiment, although it is contemplated that anchor extension 30 could be replaced with a second anchor extension 100. It is further contemplated that a single anchor extension or three or more anchor extensions 30 and/or 100 could be provided for engagement with a corresponding number of anchors, such as anchors 80 shown in FIGS. 28-31.

Figure 31:
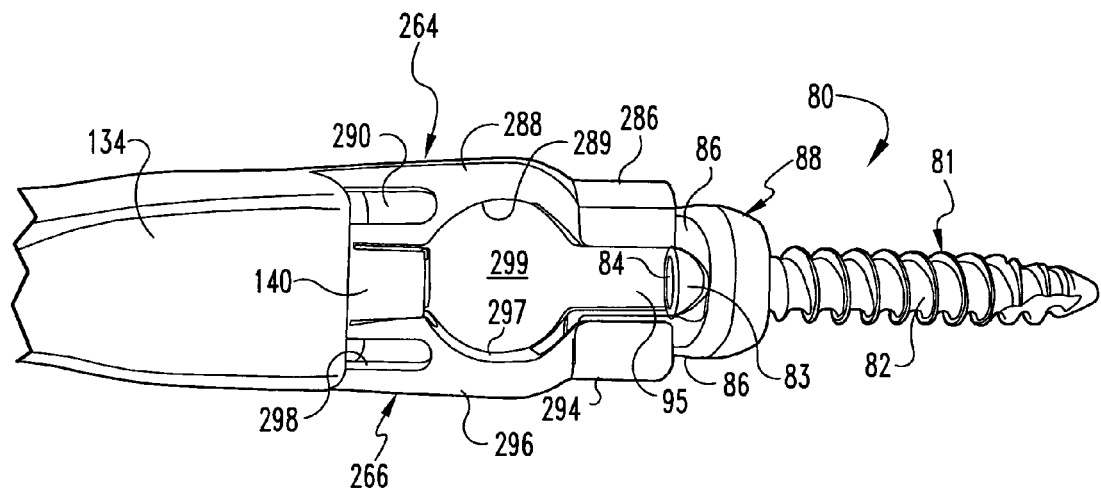
FIG. 31 is an elevation view of a distal portion of another embodiment for the anchor extension of FIG. 7.

As further shown in FIG. 31, anchor 80 can include a screw portion 81 with bone engaging threads formed on shank 82 and a head 83 that includes tool opening 84, such as a hex opening or the like, configured to receive a driving tool. In the illustrated embodiment, anchor 80 is a multi-axial screw assembly that has a receiver to receive connecting element 90 in the form of yoke 88 pivotably coupled to head 83 of screw portion 81. However, the use of an anchor 80 that does not include a screw having multi-axial capabilities is not precluded. As is known in the art, screw portion 81 is capable of being pivoted within yoke 88 to assume a plurality of angles relative thereto, and rotated relative to yoke 88 to engage bony structure with the threaded shank 82. Further examples of multi-axial screws are described in U.S. Pat. Nos. 5,797,911 and 5,879,350, each of which is incorporated herein by reference.

Other embodiment anchors are also contemplated. Anchor 80 can be in the form of a bone screw, bolt, staple, hook, tack, saddle, or interbody device, for example. Anchor 80 can be provided with a receiver to receive connecting element 90 and secure it to the bony structure.

Figure 36:
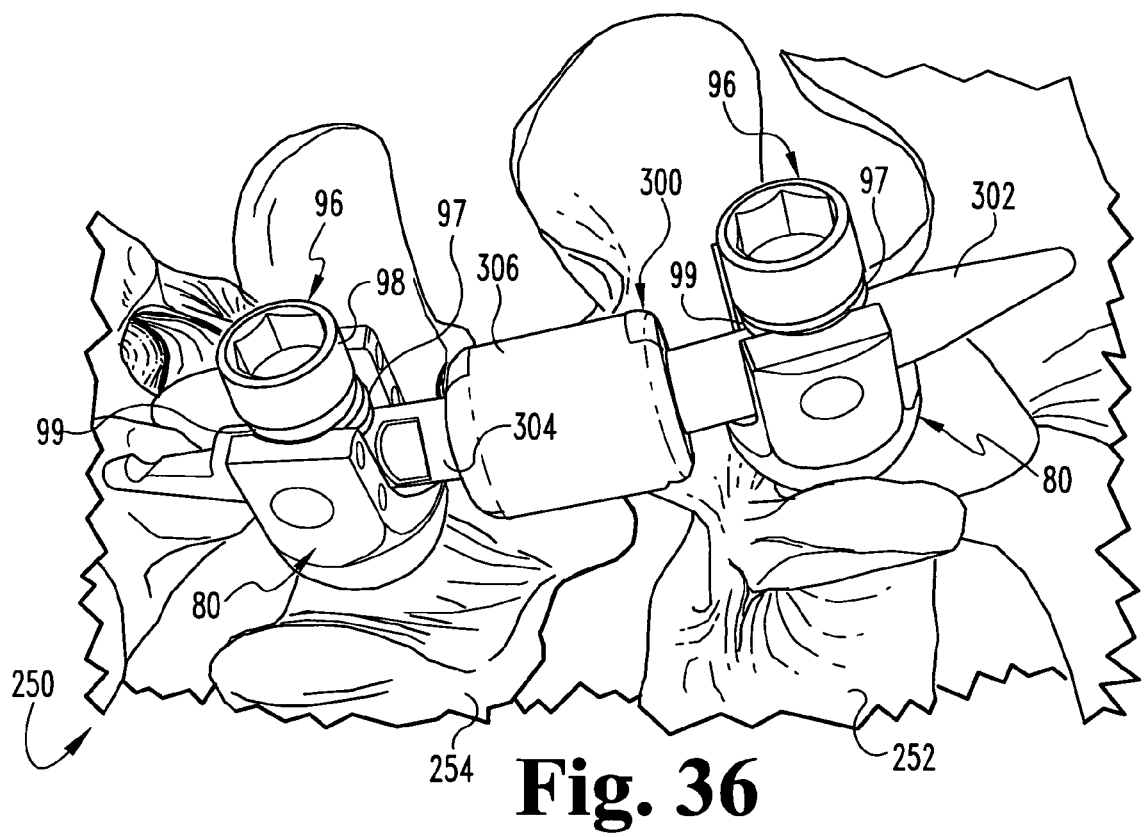
FIG. 36 is a perspective view of the spinal column segment of FIG. 35 with the anchor extensions removed and the connecting element secured to the first and second anchors.

In the illustrated example, anchor 80 includes a connector in the form of yoke 88 having passageway 95 therethrough for receiving connecting element 90. Head 83 of screw portion 81 is received within and captured at the bottom of yoke 88. Yoke 88 includes arms 86 extending proximally along and positioned on opposite sides of passageway 95. Arms 86 can have internal threads configured to mate with an externally threaded distal portion 97 of set screw 96 (FIG. 36.) Set screw 96 has proximal tool engaging portion 98, and a shoulder 99 between portions 97, 98 that is carried by one of the members of anchor extensions 30, 100. Set screw 96 is positioned with shoulder 99 supported by the anchor extension, and is released by threading distal portion 97 past the supporting member of the anchor extension. Proximal portion 98 can further be configured to break-off from distal portion 97 when a predetermined threshold torque is applied at proximal tool engaging portion 98, thus allowing a pre-determined and uniform securing force to be applied to connecting element 90 with each of the set screws 96. When employed with anchor extension 30, set screw 96 is released when proximal portion 98 is severed.

Connecting element 90 includes a length between a connecting end 91 and an insertion end 92 sufficient to interconnect at least two anchors 80. Connecting element 90 can be an elongated rod or shaft curved along its length between ends 91, 92 with a radius of curvature R. However, it should be understood that connecting element 90 can include any configuration known for a rod, implant, or fastener. For example, connecting element 90 can be a rigid member, or an elastic or super-elastic member in the form of a cable, band or artificial ligament that used in tethering or other surgical procedures. Connecting element 90 can be percutaneously or non-percutaneously inserted with an installation instrument 20 into passageways of anchors engaged to a bony structure in the body of an animal subject to stabilize the bony structure.

In the illustrated embodiment, inserter 24 includes a distal arm 31 curved at a single radius R along an arc A, and connecting element 90 has an axis co-linear with arc A. However, it is contemplated that connecting element 90 can have a curvature that differs from arc A, or can have a curvature that varies or is compounded along its length. The curvature of connecting element 90 can be defined by any one or any combination of mathematical relationships, including, for example, linear, exponential, logarithmic, trigonometric, geometric, parabolic, quadratic, cubic, hyperbolic, elliptic, or parametric relationships.

Connecting element 90 in FIG. 1 is guided into the body of the patient via inserter 24. The installation instrument can employ any type of fixed geometric relationship to insert connecting element 90 toward the anchors engaged to the bony structure of the patient. This fixed geometric relationship can be governed any one or combination of a pinned joint, a cam, a four-bar linkage, or a guide member that provides a path for translational movement of connecting element 90, for example. Inserter 24 can be mounted to a single anchor extension, or to three or more anchor extensions. Connecting element 90 can further be guided and positioned in the patient with free hand techniques, image guidance techniques, or with other suitable instruments.

Referring now to FIGS. 2-5, further details of one embodiment of anchor extension 30 are shown. Anchor extension 30 includes an inner sleeve 50 that is received proximally within a bore 45 of outer sleeve 40. Inner sleeve 50 defines a bore 51 therethrough that allows tools to extend to the anchor. Distal end 53 of inner sleeve 50 includes a lip 52 extending radially therearound projecting into inner bore 51. Lip 52 can support a set screw, such as set screw 96 discussed above, on lip 52 adjacent distal end 53 of inner sleeve 50.

Figure 2:
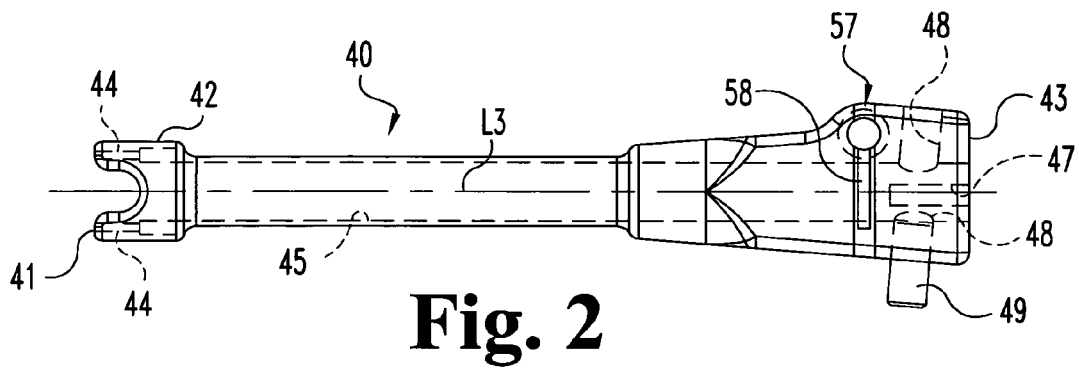
FIG. 2 is an elevation view of one of the anchor extensions of the installation instrument of FIG. 1.
Figure 3:
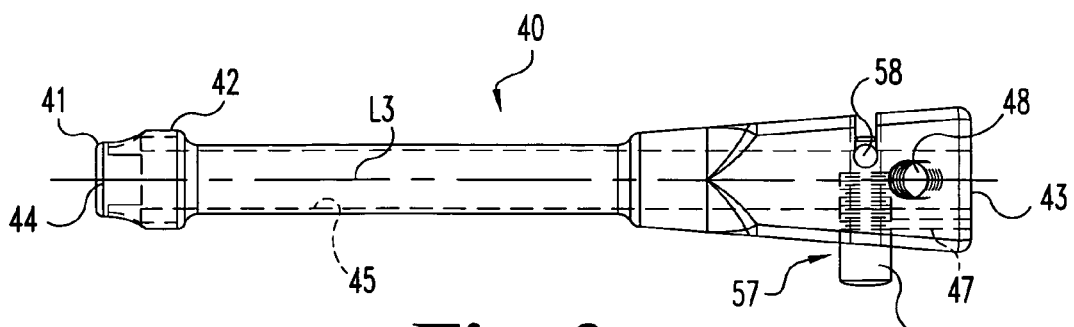
FIG. 3 is an elevation view of the anchor extension of FIG. 2 rotated 90 degrees about its central axis.

Outer sleeve 40 includes an end portion 42 at distal end 41 thereof. As shown in FIG. 2, end portion 42 has a U-shaped opening to accommodate insertion of connecting element 90 therethrough. A pair of opposing arms 44 of end portion 42 are alignable with the arms 86 of yoke 88 to receive arms 86 therein with passageway 95 aligned with the passage between arms 44.

When assembled, a longitudinal axis L1 of outer sleeve 50 is alignable with a longitudinal axis L3 of inner sleeve 40. An alignment pin 63 of inner sleeve 50 is received in slot 47 of outer sleeve 40 to ensure and maintain proper alignment of inner sleeve 50 in outer sleeve 40. Anchor extension 30 further includes a receptacle 48 extending laterally therethrough transversely to longitudinal axis L3. Receptacle 43 opens laterally adjacent the proximal end 43, and receives a pin from inserter 24 to mount inserter 24 to anchor extension 30. A coupling pin 49 is press fit or otherwise secured in receptacle 48 opposite the laterally opening receptacle to provide a medially extending pin to facilitate coupling of anchor extension 30 with anchor extension 100.

Inner sleeve 50 includes lower gripping elements or fingers 54 that include circular relief portions 77 therebetween to allow flexing of fingers 54. Shoulder 61 limits the depth of travel of inner sleeve 50 distally into bore 45 of outer sleeve 40. Inner sleeve 50 further includes distal and proximal notches 56a, 56b extending transversely to longitudinal axis L1, and spaced proximally of fingers 54 and distally of proximal end 55. Outer sleeve 40 includes a plunger-type spring biased retainer 57 extending therein adjacent bore 45 having a cross bar 58 extending transversely from a plunger 59. Cross bar 58 is selectively positionable in a desired one of the notches 56a, 56b to hold inner sleeve 50 in a selected position relative to outer sleeve 40.

When cross-bar 58 is in the proximal notch 56b, lip 52 of inner sleeve 50 projects into space between arms 42 of outer sleeve 40. Set screw 96 is supported by lip 52, and its lower threaded portion extends between arms 44. If not already secured to set screw 96, yoke 88 can then be at least partially threaded onto set screw 96. Movement of inner sleeve 50 relative to outer sleeve 40 is facilitated by depressing plunger 59 to lift cross bar 58 out of proximal notch 56b. Inner sleeve 50 is moved proximally to position cross bar 58 in the distal notch 56a, drawing yoke 88 between the arms 44 and against end portion 42 with passage 70 aligned with the U-shaped opening between the arms 44. When cross bar 58 is in distal notch 56a, arms 86 of anchor 80 are drawn proximally between arms 44 of outer sleeve 40. Arms 44 define a passage therebetween adapted to receive arms 86 of yoke 88 in form-fitting engagement and firmly secure yoke 88 of anchor 80 to anchor extension 30. However, yoke 88 remains pivotal relative to screw portion 81 to allow anchor extension 30 to be re-positioned for coupling with anchor extension 100 and inserter 24.

Figure 6:
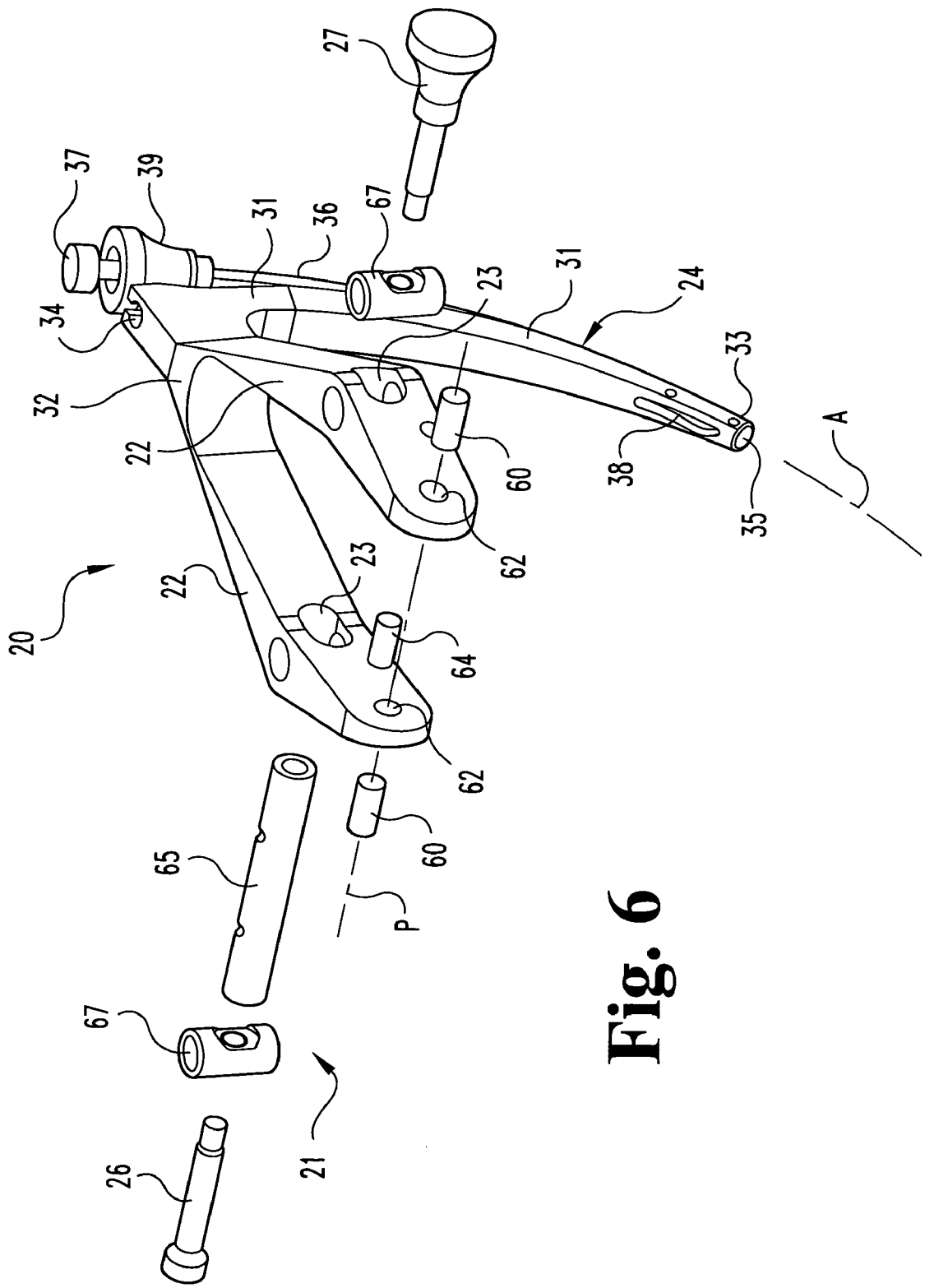
FIG. 6 is a perspective view of an inserter comprising a portion of the installation instrument of FIG. 1.

As shown in further detail in FIG. 6, installation instrument 20 includes an inserter 24. Further details regarding inserter 24 and techniques for it are provided in U.S. Pat. No. 6,530,929, which is incorporated herein by reference in its entirety. Inserter 24 includes first and second support arms 22. Support arms 22 come together and are fixedly connected at a proximal end 32 of distal arm 31. Distal arm 31 includes a distal end 33 from which connecting element 90 extends. Inserter 24 includes a coupling member 38 adjacent distal end 33 for securing connecting element 90 thereto. Inserter 24 is pivotable about a pivot axis P to define a curvilinear arc or insertion axis A. Distal arm 31 of inserter 24 is preferably curved to follow axis A and facilitate smooth percutaneous insertion and withdrawal of distal arm 31 and the connecting element 90 coupled thereto.

Coupling member 38 is pivotally mounted to distal arm 31, and movable thereto by manipulating thumb knob 37. Coupling member 38 is in communication with a distal opening 35 in distal end 33 that extends proximally therefrom. Coupling member 38 releasably engages connecting element 90 in distal opening 35.

Distal arm 31 includes a channel 34 extending from distal end 33 therealong toward proximal end 32. Channel 34 receives a coupler 36 therein that is secured to inserter 24 by a nut 39. For the purposes of clarity, nut 39 and coupler 36 are shown displaced from channel 34 in FIG. 6 except at distal end 33. Coupler 36 is an elongated flexible member that extends with insertion axis A from distal end 33 through nut 39 to a thumb knob set screw 37 adjacent proximal end 32. Set screw 37 is threadingly received in a threaded opening formed in nut 39. Coupler 36 is pivotably coupled to coupling member 38, and is operable with thumb knob set screw 37 to move coupling member 38 to engage and release connecting element 90 to inserter 24. Connecting element 90 is positionable in distal opening 35 so that connecting element 90 is relatively fixed with respect to inserter 24 by coupling member 38, maintaining alignment of connecting element 90 along insertion axis A during insertion of connecting element 90. In order to grip and release connecting element 90 in opening 35, coupling member 38 is selectively actuated by drawing coupler 36 distally and proximally via threading of thumb knob 37 relative to lock nut 39.

Support arms 22 have through-holes 23 for receiving a clamping mechanism 21. Clamping mechanism 21 draws arms 22 toward one another to pivotably secure anchor extensions 30, 100 therebetween. Pivot nuts 67 are positionable in respective ones of the holes 23. A clamping bar 65 extends between arms 22, and has threaded bores at each end that allow bar 65 to be secured to and clamp arms 22 via threaded fastener 26 and a threaded end of clamping knob 27. Clamping knob 27 is manipulated by the surgeon to secure or release extensions 30, 100 from between arms 22.

In the illustrated embodiment, pins 60 are press fit into respective ones of the openings 62 of arms 22. Anchor extensions 30, 100 are rotatably mounted on adjacent ones of the support arms 22 via the adjacent pin 60 extending into laterally opening receptacles of the anchor extensions, such as receptacle 48 discussed above. Each arm 22 can be provided with a stop bar 64 extending therefrom towards the opposite support arm 22. Stop bars 64 limit rotation of inserter 24 along insertion axis A when a stop bar 64 contacts a corresponding one of the extensions 30, 100.

Figure 10:
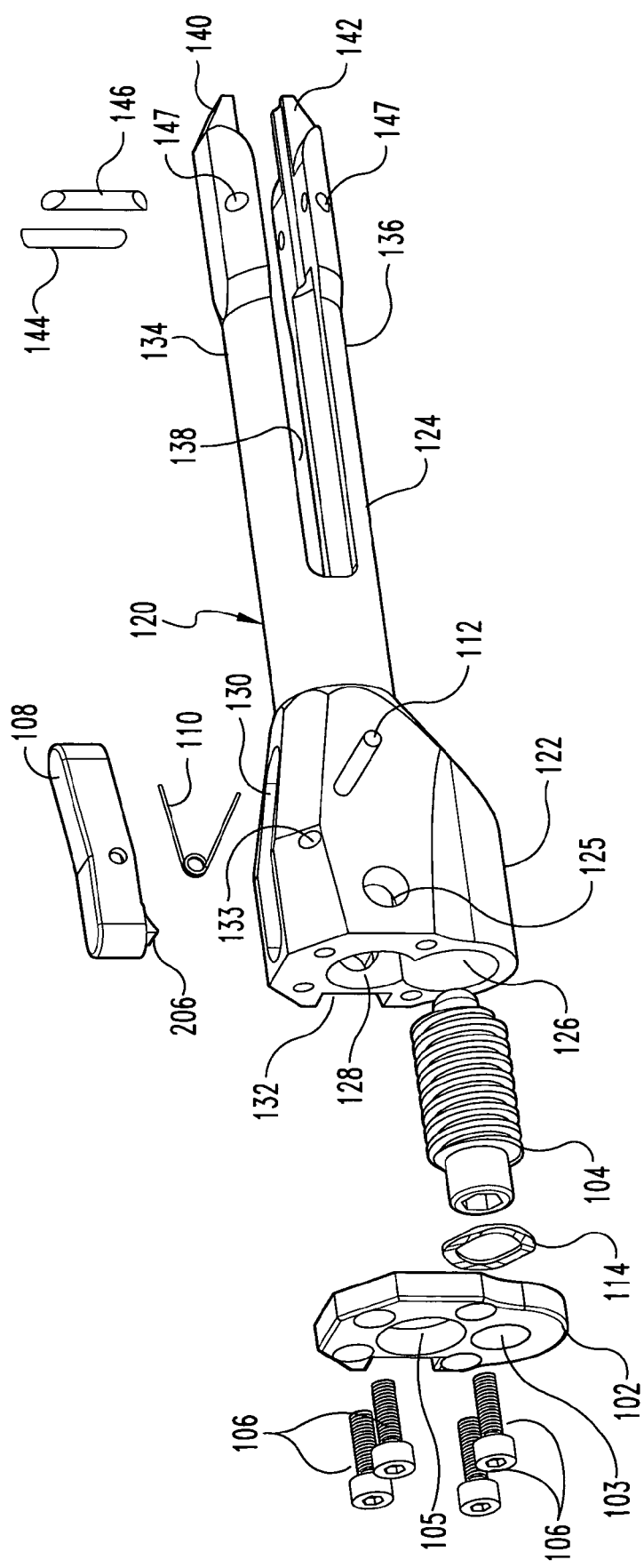
FIG. 10 is an exploded view of the anchor extension of FIG. 7 with an inner member removed from an outer member thereof.
Figure 11:
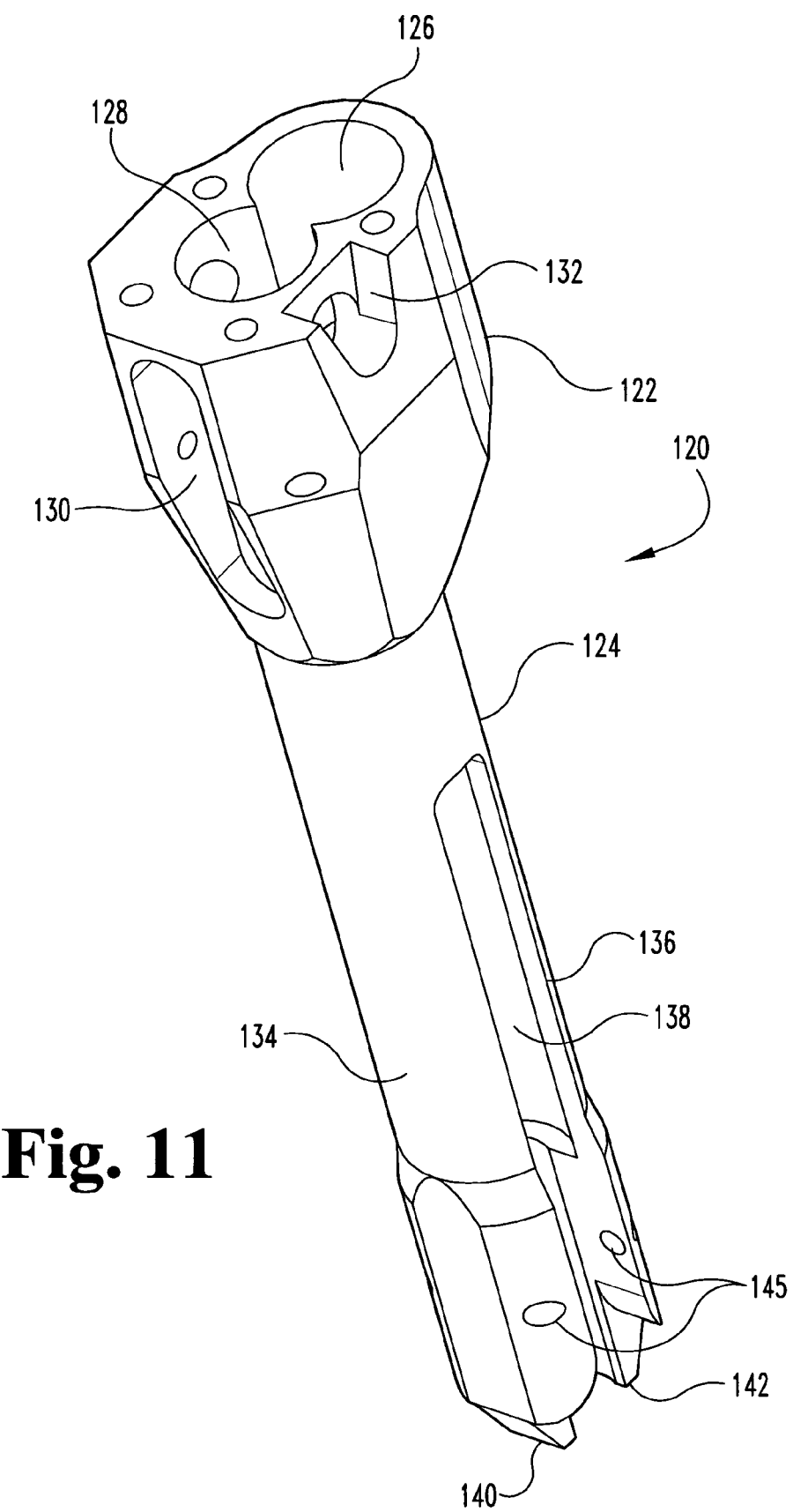
FIG. 11 is a perspective view of the outer member of the anchor extension of FIG. 7.

Referring now to FIGS. 7-16, further details of anchor extension 100 are shown. In FIGS. 7-9 anchor extension 100 is shown in an assembled form. Anchor extension 100 includes a first member 120 in the form of an outer sleeve and a second member 160 movably received in first member 120. As further shown in FIGS. 10-12, first member 120 includes an enlarged proximal housing portion 122 and a distal portion 124. Proximal housing portion 122 includes a medial receptacle 125 and an opposite lateral receptacle 132 (FIG. 11.) When assembled with inserter 24 and anchor extension 30, medial receptacle 125 receives coupling pin 49, and lateral receptacle 132 receives a pin 60 of inserter 24. Medial receptacle 125 can include a flared recessed portion extending proximally to facilitate placement of pin 60 therein.

Figure 12:
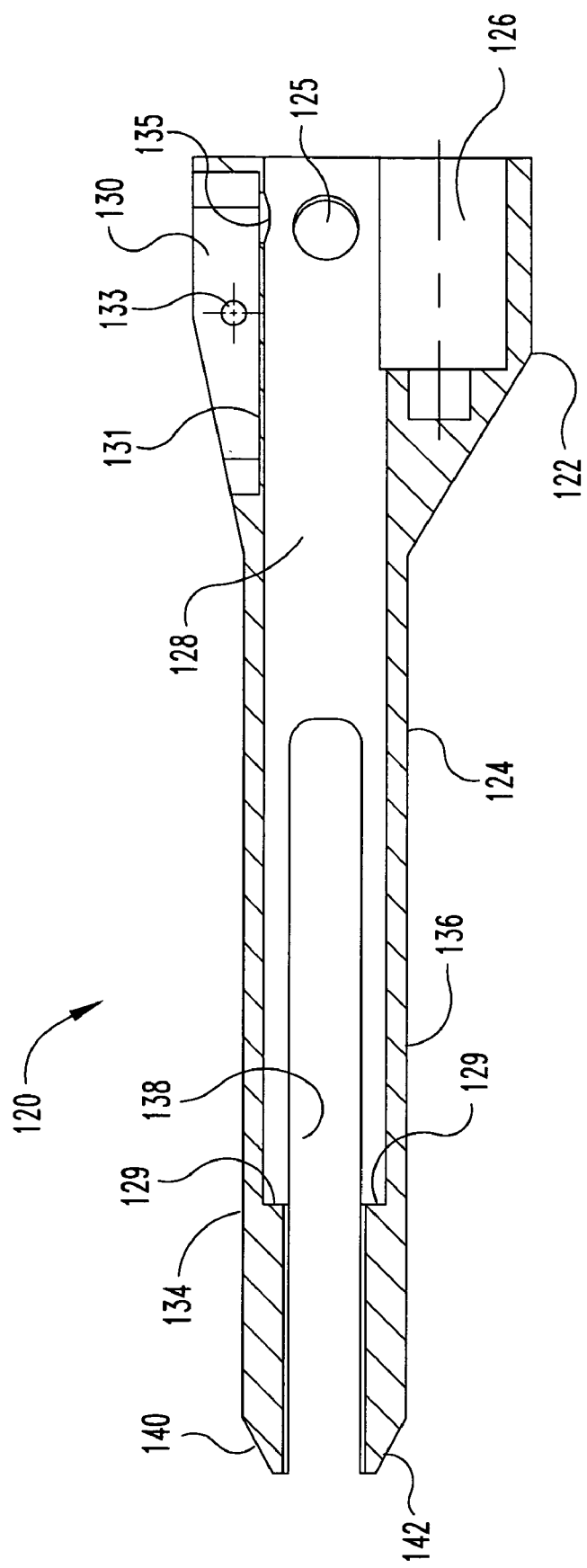
FIG. 12 is a cross-sectional view along the longitudinal axis of the outer member of FIG. 11.
Figure 13:
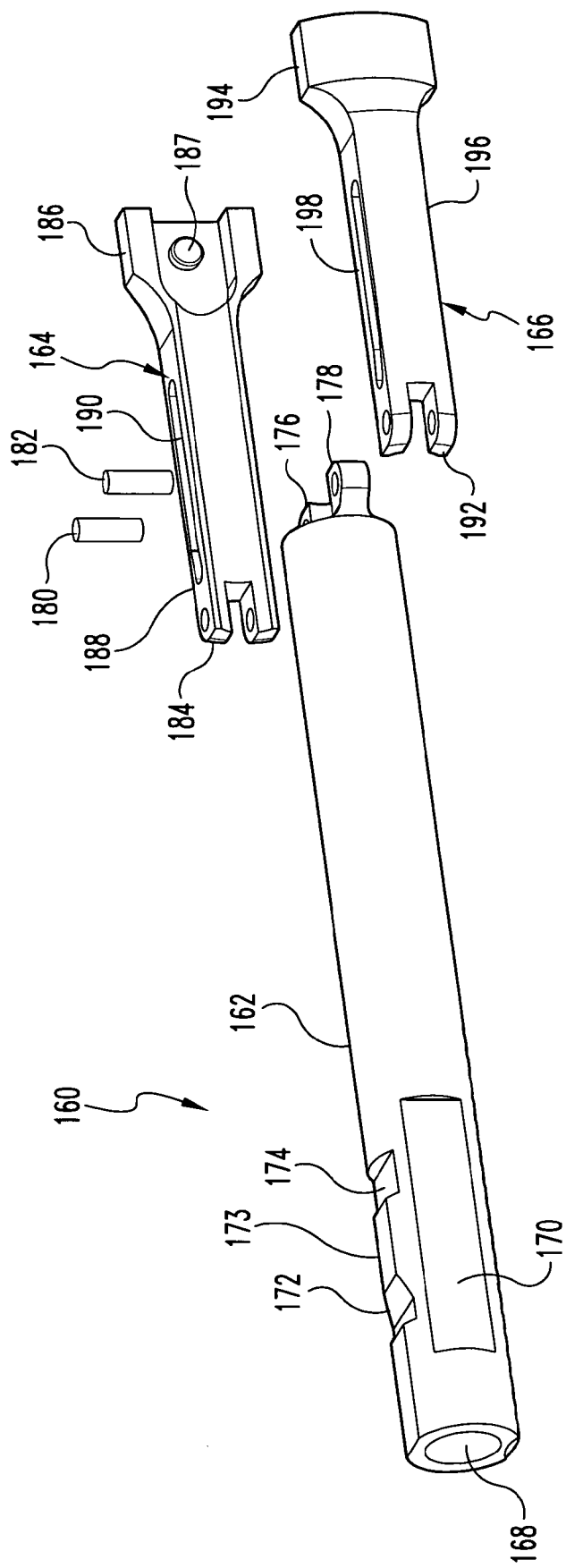
FIG. 13 is an exploded view of the inner member of the anchor extension of FIG. 7.

In FIG. 10, anchor extension 100 is shown in an exploded view with second member 160 removed, and in FIG. 11 first member 120 is shown in a perspective view and in a section view in FIG. 12. First member 120 further includes a passage 128 extending between and opening at the proximal and distal ends thereof sized to receive second member 160 therein. First member 120 includes a drive member receptacle 126 in proximal housing portion 122 which opens toward a proximal end thereof, and is in communication with passage 128. A drive member 104 is positionable in receptacle 126 and engageable to second member 160 to move second member 160 relative to first member 120, as discussed further below.

Proximal housing portion 122 further includes a lock receptacle 130 in proximal housing portion 122 opposite drive member receptacle 126. Lock receptacle 130 includes holes 133 to receive a lock pin 112 therein. Lock receptacle 130 further includes a recessed wall 131 extending therealong to an opening 135. Opening 135 is in communication with passage 128. A locking mechanism includes lock button 108 pivotally coupled to proximal housing portion 122 in receptacle 130 with lock pin 112. A spring 110 biases lock member 108 to a locked position, as discussed further below.

A cap 102 is engageable to the proximal end face of first member 120 with fasteners 106. Cap 102 captures drive member 104 in drive member receptacle 126, while spring washer 114 maintains contact between drive member 104 and cap 102 to prevent drive member 104 from floating in receptacle 130. Drive member 104 includes a tool engaging receptacle at its proximal end, and cap 102 includes a first opening 103 to provide access to the tool engaging receptacle. Cap 102 further includes a second opening 105 through which a proximal end portion of inner sleeve 160 extends.

Distal portion 124 of first member 120 includes a first arm 134 and a second arm 136 with a slot 138 therebetween. First arm 134 includes a first reducing member 140, and second arm 136 includes a second reducing member 142. Reducing members 140, 142 are spaced from one another on opposite sides of slot 138 at the distal ends of arms 134, 136. Reducing members are tapered distally and include a wedge-shape and fit between the distal ends of jaws 164, 166 when in a reduction configuration. First and second arms 134, 136 include aligned holes 145, 147 on opposite sides thereof. As discussed further below, first arm 134 and second arm 136 are attachable to jaws 164, 166 of inner member 160 with guide pins 144, 146 positionable through holes 145, 147. As shown in further detail in FIG. 12, first member 120 includes passage 128 forming an internal lip 129 about first arm 134 and second arm 136. The distal end of sleeve 162 of second member 160 contacts lip 129 to limit displacement of second member 160 distally relative to first member 160

As shown in FIGS. 13-16, second member 160 includes a proximal sleeve portion 162. First jaw 164 and second jaw 166 are pivotally coupled to first ear 176 and second ear 178 at a distal end of proximal sleeve portion 162 with first and second pins 180, 182, respectively. Proximal sleeve portion 162 includes a passage 168 extending therethrough and opening at the proximal and distal ends of sleeve portion 162. Proximal sleeve portion 162 includes an engagement surface 170 along a portion thereof engageable by drive member 104. Engagement surface 170 can comprise a series of threads which interdigitate with threads of drive member 104 such that as drive member 104 is rotated, first member 120 is moved distally or proximally relative to second member 160, depending on the direction of rotation of drive member 104. Proximal sleeve portion 162 further includes a proximal notch 172 and a distal notch 174 for engagement by lock button 108.

First jaw 164 includes a proximal coupling portion 184 to receive first pin 180 and pivotally couple first jaw 164 to first ear 176. Similarly, second jaw 166 includes a proximal coupling portion 192 to receive second pin 182 and pivotally couple second jaw 166 to second ear 178. First jaw 164 includes a distal anchor coupler 186, and a protrusion 187 extending medially therefrom. First jaw 164 includes a body 188 extending proximally from anchor coupler 186, which includes a guide slot 190 extending therethrough. Similarly, second jaw 166 includes a distal anchor coupler 194, and a protrusion (not shown) extending therefrom toward protrusion 187. Second jaw 166 includes a body 196 extending proximally from anchor coupler 194, which includes a guide slot 198 extending therethrough. Guide pins 144, 146 extend through respective ones of the guide slots 190, 198 to couple jaws 164, 166 to respective ones of the arms 134, 136.

Figure 19:
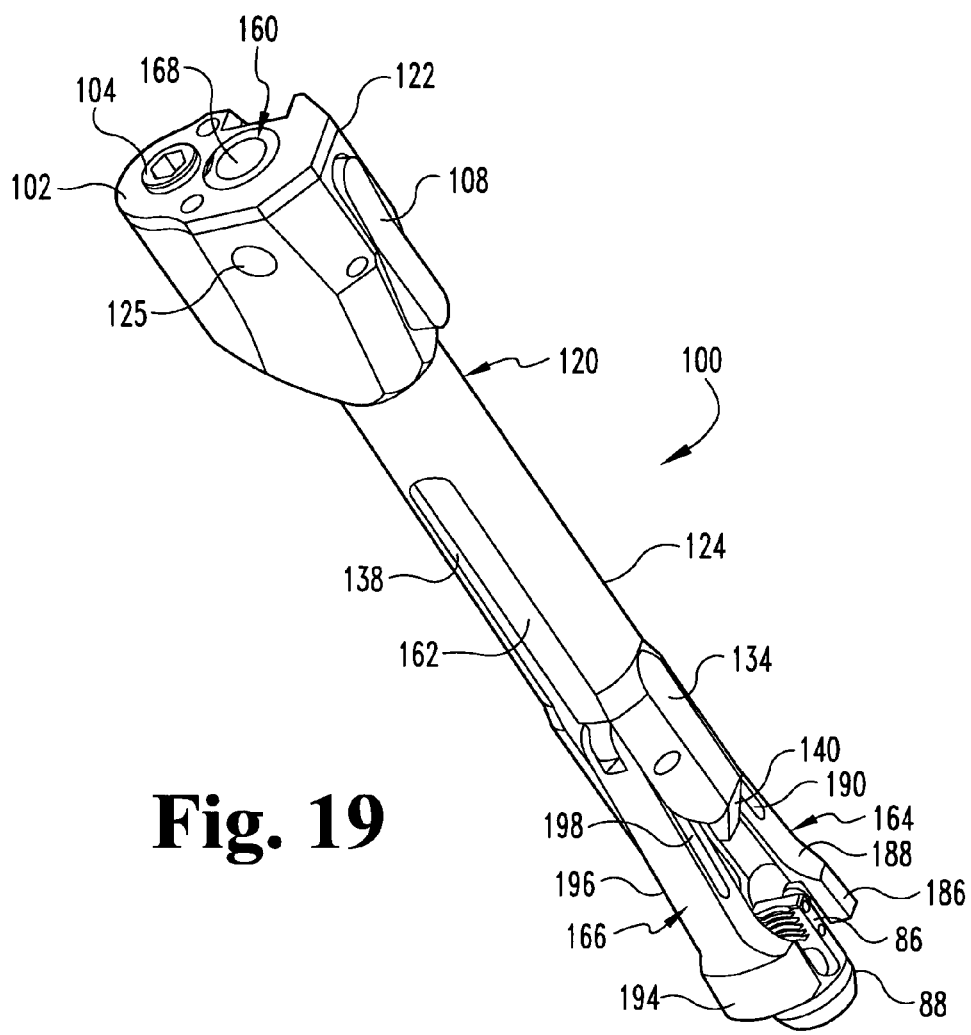
FIG. 19 is a perspective view of the anchor extension of FIG. 7 in an unlocked condition being positioned over the head of an anchor.
Figure 21:
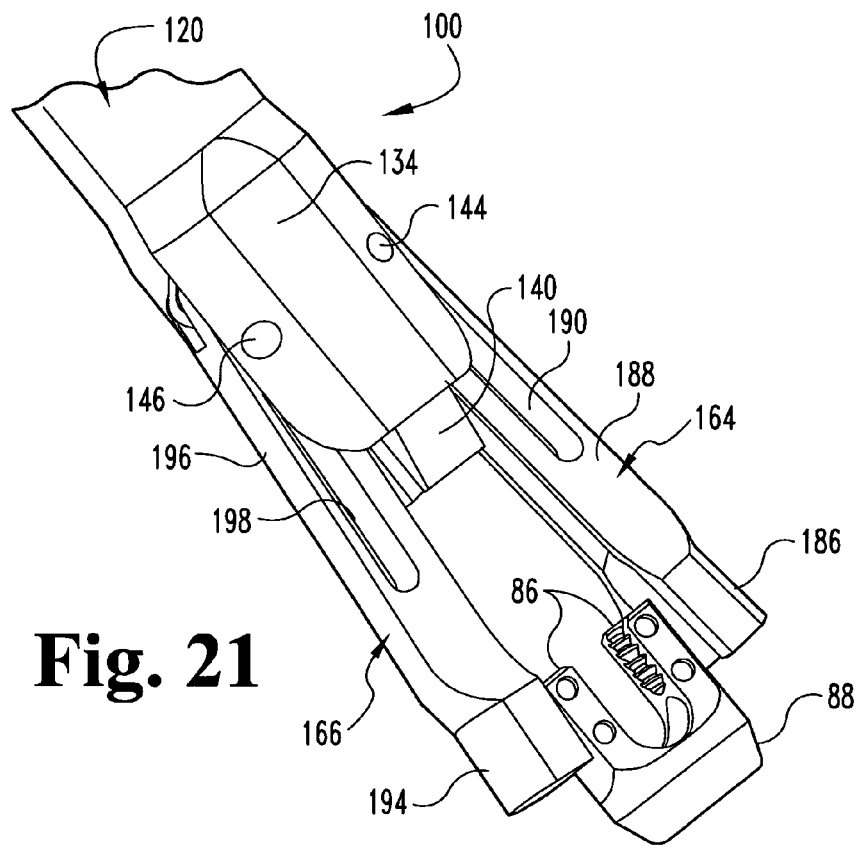
FIG. 21 is an enlarged perspective view of a distal portion of the anchor extension and anchor head of FIG. 19.

Further details of jaws 164, 166 are shown in FIGS. 15-16 with respect to jaw 164, it being understood that jaw 166 is an identical mirror image. Slots 190, 198 each include a proximal cammed portion 191 extending proximally toward one another so that guide pins 144, 146 force anchor couplers 186, 194 away from one another when second member 160 is displaced distally relative to first member 120 with drive member 104, as shown in FIGS. 19 and 21. Slots 190, 198 extend parallel to one another distally of cammed portion 191, so that when second member 160 is moved proximally relative to first member 120, guide pins 144, 146 move into the parallel slot portions and move anchor couplers 186, 194 toward one another to grip arms 86 of anchor 80 therebetween. In the gripping position, jaws 164, 166 form a passage therebetween sized to permit placement of connecting element 90 therethrough along insertion axis A.

As shown in further detail in FIGS. 17 and 18, lock button 108 includes a body with a proximal portion 200 and a distal portion 202. Proximal portion 200 is angled at angle 212 relative to distal portion 202 to facilitate access to button 108 and provide a more positive visual indication of the button positioning relative to housing portion 122. Lock button 108 includes a receptacle 208 opening along a bottom surface thereof. Lock button 108 includes a lock member 206 adjacent proximal portion 200 thereof projecting below the bottom surface of lock button 108.

In its assembled orientation, as shown in FIG. 10, lock button 108 is positioned in receptacle 130. Receptacle 130 includes recessed wall 131 with lock member opening 135 adjacent a proximal end thereof. Lock member 206 projects through lock button opening 135 for engagement with second member 160. Spring 110 is received in receptacle 208 and receptacle 130, and extends between lock button 108 and recessed wall 131 to bias lock member 206 through opening 135. Pin 112 is positioned through the eyelet of spring 110 and openings 210 through the sidewalls of lock button 108. Pin 112 is secured in openings 133 of proximal housing portion 122 of first member 120. Lock member 206 of lock button 108 is engageable in the notches 172, 174 as second member 160 is moved relative to first member 120, as discussed further below.

Figure 27:
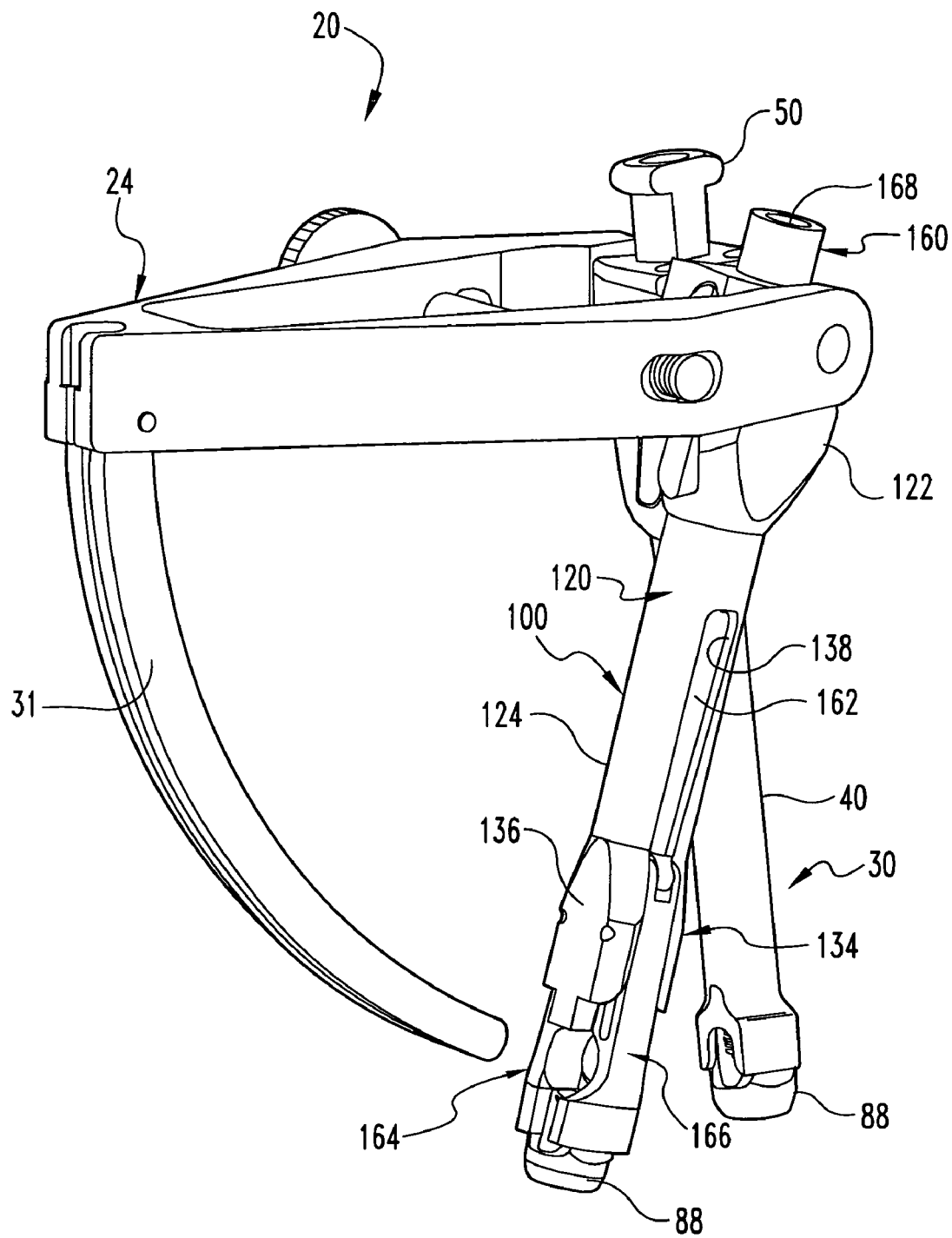
FIG. 27 is a perspective view of the installation instrument of FIG. 1 mounted to a pair of anchor heads with the connecting element removed to illustrate the passage between the jaws of the inner member of through the anchor extension of FIG. 7 to receive the connecting element.
Figure 28:
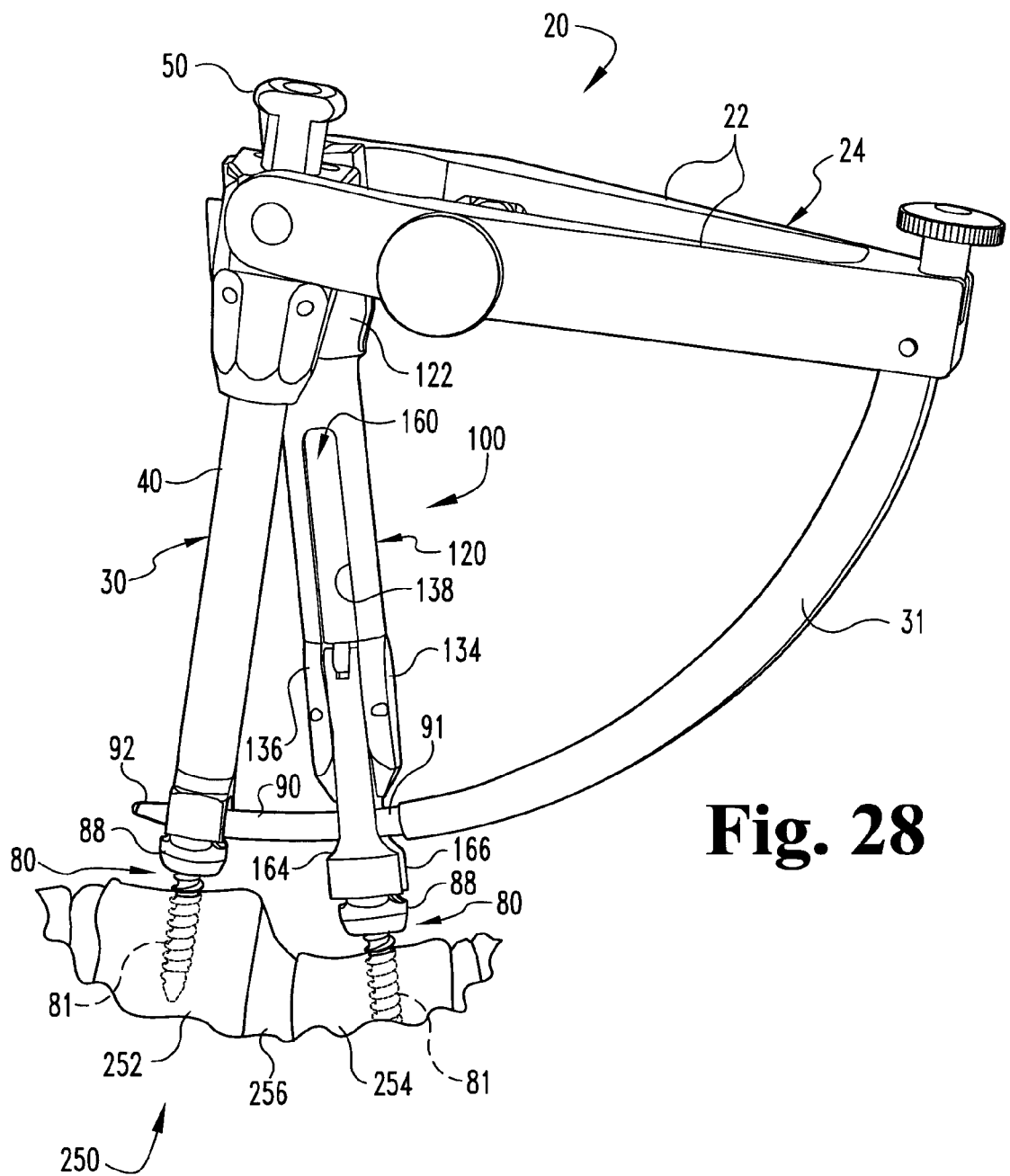
FIG. 28 is an elevation view of a spinal column segment and of the installation instrument of FIG. 27 with a connecting element coupled thereto and positioned through the anchor extension of FIG. 7 and into a receiver of a second anchor.
Figure 29:
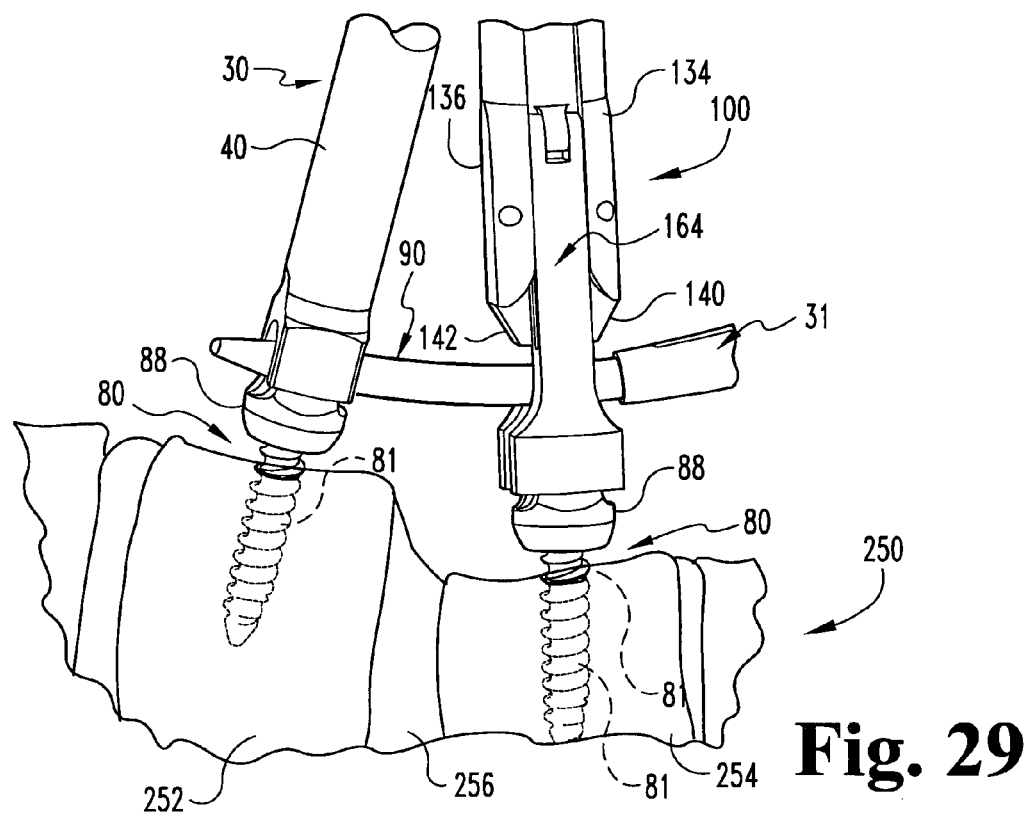
FIG. 29 is an elevation view of the distal portion of the installation instrument, connecting element and anchors of FIG. 28.

Anchor extensions 30, 100 are engageable to anchors 80. When assembled with anchor extension 30, yoke 88 is received within end portion 42 at distal end 41 of outer sleeve 40, such as shown in FIG. 27. Set screw 96 is captured on the distal end of inner sleeve 50. End portion 42 includes an internally shaped wall surface that conforms to and non-rotatably receives yoke 88 to rigidly secure yoke 88 thereto when plunger 57 is positioned in the distal notch 56a.

Figure 20:
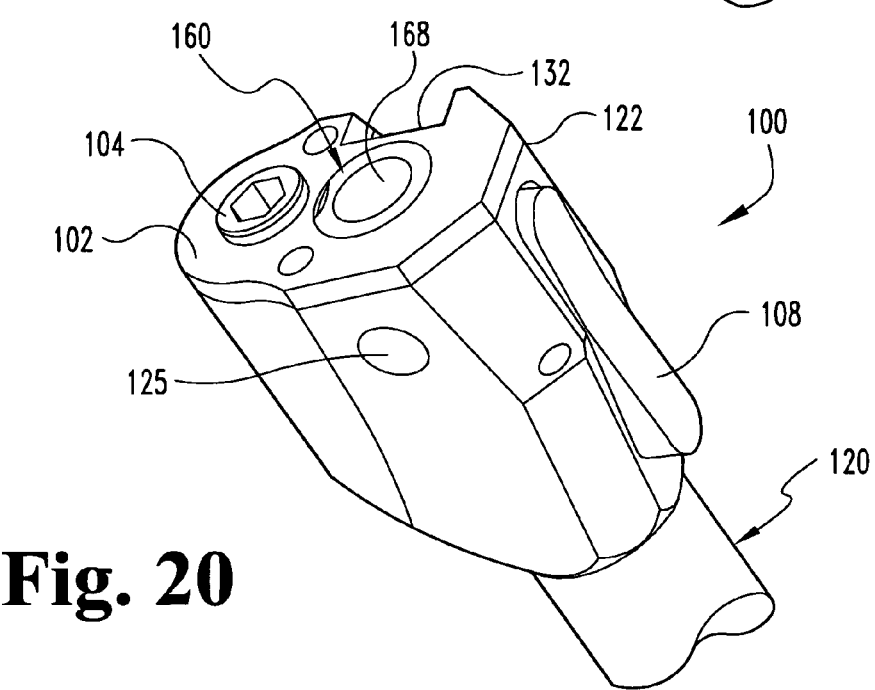
FIG. 20 is an enlarged perspective view of a proximal portion of the anchor extension of FIG. 19.

Anchor extension 100 is engaged to anchor 80 by positioning clamping jaws 164, 166 in their opened configuration on respective sides of the outer surfaces of arms 86 of yoke 88, as shown in FIGS. 19 and 21. In this position, second member 160 is displaced as far as possible distally relative to first member 120, as shown in FIG. 20. Guide pins 144 are received in the proximal cammed portions 191 of slots 190, 198, forcing anchor couplers 186, 194 away from one another so that arms 86 of yoke 88 can be positioned between anchor couplers 186, 194.

As shown in FIG. 20, when jaws 164, 166 are in their open configuration of FIGS. 19 and 21, lock button 108 is rotated clockwise and positioned relative to proximal housing portion 122 to indicate that lock member 206 contacts an outer surface of inner member 160 at a location proximal of proximal notch 172. The proximal end of second member 160 is positioned flush with the proximal end surface of cap 102 engaged to first member 120.

Figure 22:
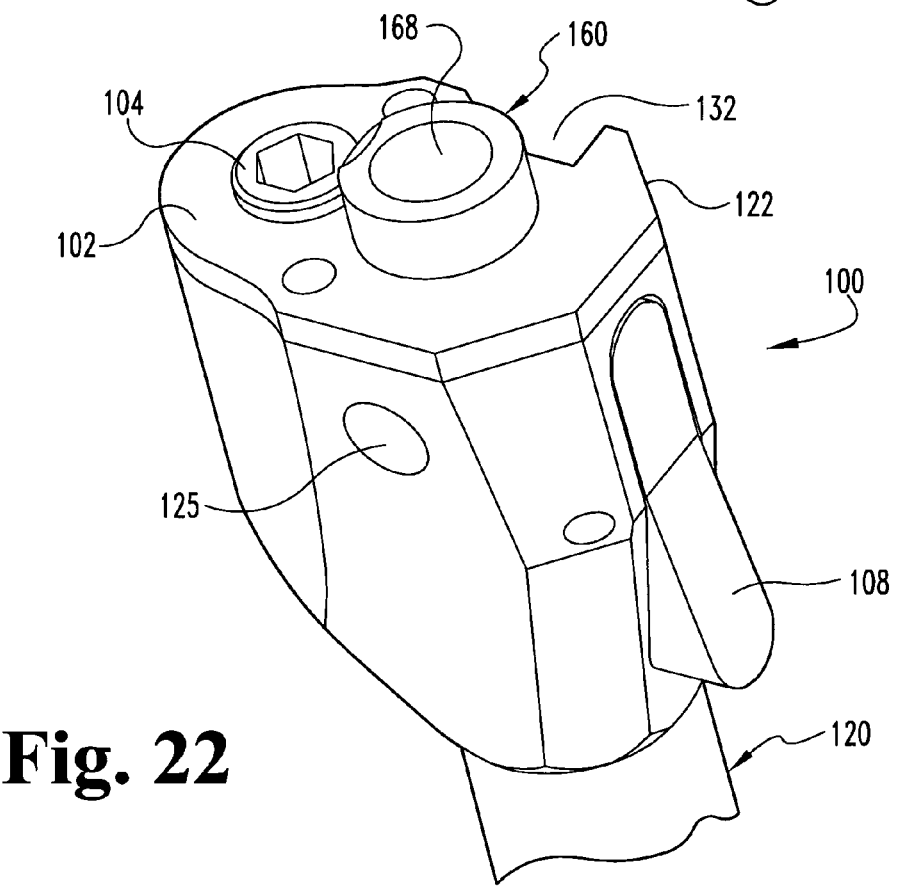
FIG. 22 is a perspective view of the proximal portion of the anchor extension of FIG. 19 in a locked condition.
Figure 23:
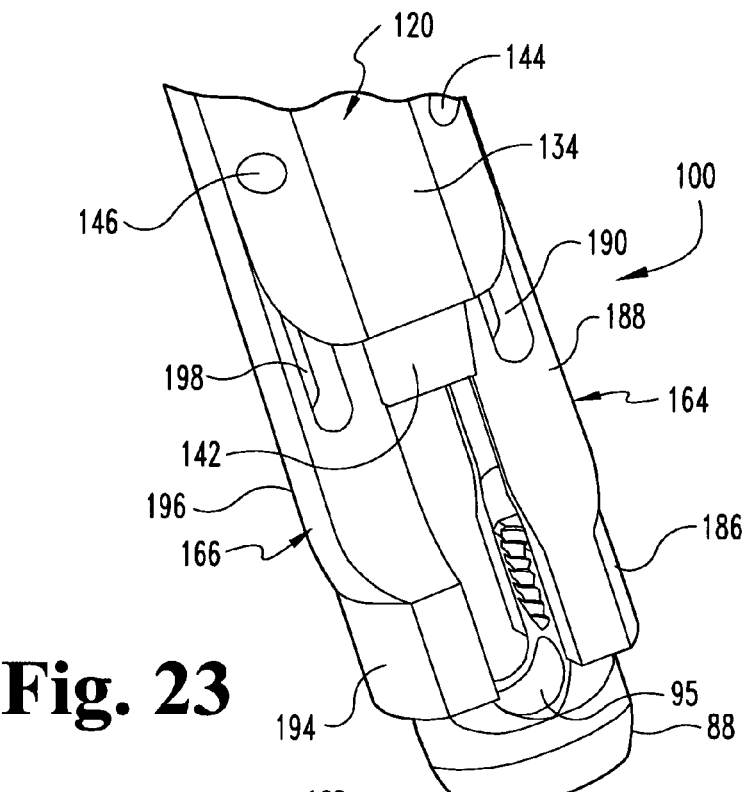
FIG. 23 is a perspective view of the distal portion of the anchor extension of FIG. 19 in a locked condition on the head of the anchor.

In FIGS. 22-23, anchor extension 100 is shown in a mounting configuration for engagement with an anchor, such as anchor 80. In this configuration first member 120 is in an intermediate position relative to second member 160 so that guide pins 144, 146 are located at the proximal ends of the parallel portions of slots 190, 198. Jaws 164, 166 are biased toward one another to grip arms 86 of yoke 88 between anchor couplers 186, 194. However, reducing members 140, 142 are spaced proximally from anchor 80 a sufficient distance to permit placement of connecting element 90 through the passage between jaws 164, 166 at a location along insertion axis A between reducing members 140, 142 and the proximal end of anchor 80.

In this intermediate position, the proximal end of second member 160 projects proximally from first member 120. Second member 160 is positioned relative to first member 120 so that lock member 206 of lock button 108 is received in proximal notch 172 of second member 160. Spring 110 can bias lock button 108 counter-clockwise so that lock member 206 is automatically received in proximal notch 172 when aligned therewith. In this intermediate position, proximal portion 200 is flush with proximal housing portion 122 of first member 120, as shown in FIG. 22. It is contemplated that an audible click can be provided by the contact of lock member 206 with the outer surface of second member 160, providing an indication that anchor 80 is secured between anchor couplers 186, 194 of jaws 164, 166.

Figure 24:
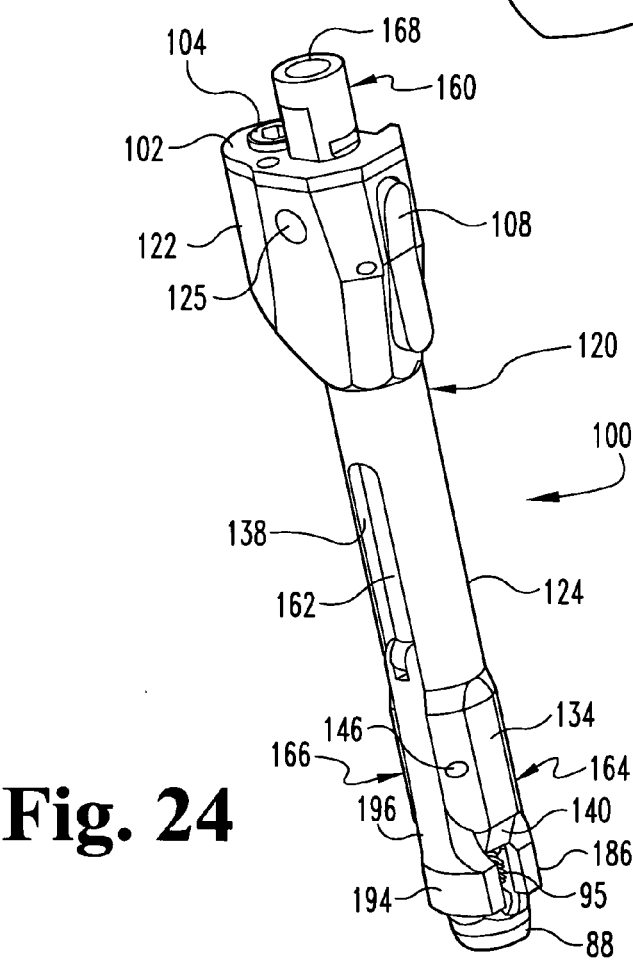
FIG. 24 is a perspective view of the anchor extension of FIG. 19 in a locked condition on the head of the anchor.

In FIG. 24 there is shown anchor extension 100 moving toward a reduced configuration in which second member 160 is proximally displaced relative to first member 120 to move reducing members 140, 142 distally and into contact with the connecting element. Drive member 104 can be rotated with a driving tool or the like to facilitate application of the necessary force to move first and second members 120, 160 relative to one and to displace the bony structure to which anchor extension 100 is engaged. Guide pins 144, 146 move distally along the parallel portions of guide slots 190, 198. Lock member 206 of lock button 108 is moved along an intermediate notch portion 173 (FIGS. 13-14) of second member 160. This in turn pushes against the bias of spring 110 and positions proximal portion 200 of lock button 108 away from proximal housing portion 122 of first member 120 such that it is no longer flush therewith.

Figure 25:
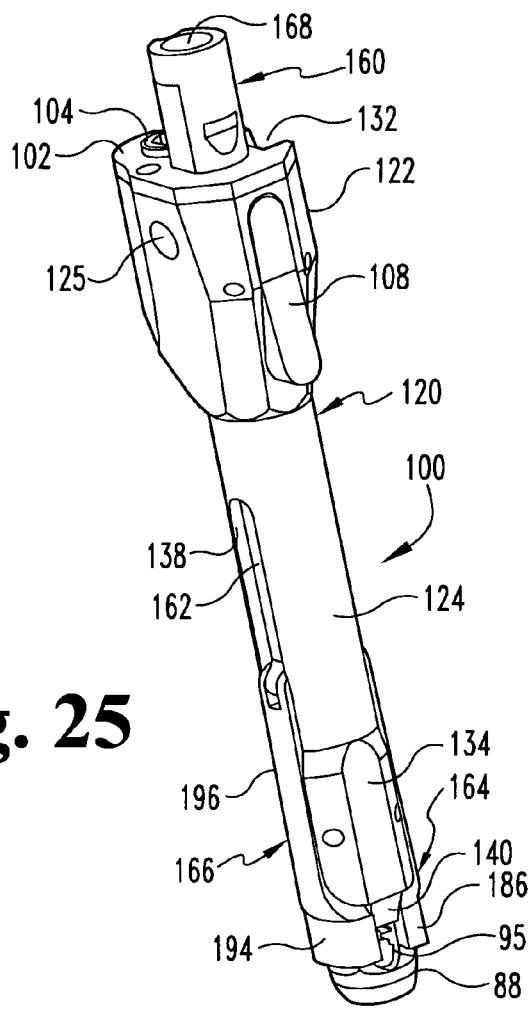
FIG. 25 is a perspective view of the anchor extension of FIG. 19 in a locked condition on the head of the anchor and the inner and outer members displaced relative to one another for reduction.
Figure 26:
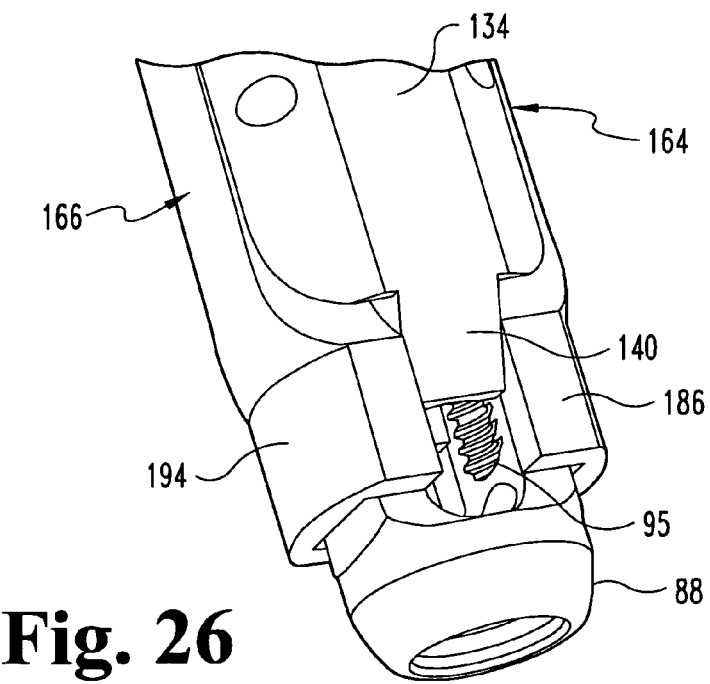
FIG. 26 is a perspective view of a distal portion of the locked anchor extension of FIG. 25 with the outer member displaced relative to the head of the anchor for reduction.

In FIGS. 25-26 there is shown anchor extension 100 in a reduced configuration in which second member 160 is completely proximally displaced relative to first member 120. In this position of second member 160, lock member 206 is received in distal notch 174, again positioning proximal portion 200 of lock button 108 flush with proximal housing portion 122 of first member 120. In the reduced configuration, reducing members 140, 142 are positioned in the passageway 95 between arms 86 of yoke 88. Second member 160 projects proximally further from the proximal end of first member 120 than in either the open or mounting configurations discussed above. Lock button 108 locks second member 160 in this reduced configuration with lock member 206 contacting the proximal end wall of distal notch 174. The positioning of lock button 108 flush with housing portion 122, and the audible click provided when lock member 206 is positioned in distal notch 174, provide an indication to the surgeon that complete reduction has been obtained. To release second member 160, distal portion 202 of lock button 108 can be pressed against the bias of spring 110 to move lock member 206 out of engagement with distal notch 174, allowing first member 120 to be displaced proximally relative to second member 160 until jaws 164, 166 release anchor 80.

FIGS. 27-30 illustrate a surgical technique employing anchor extension 100 with installation instrument 20. Anchor extension 30 and anchor extension 100 are engaged with a corresponding one of the anchors 80 engaged to vertebrae 252, 254 of spinal column segment 250. Vertebrae 252, 254 include a disc space 256 therebetween. Vertebrae 252, 254 can comprise a portion of the cervical, thoracic, lumbar and/or sacral regions of the spine. In the illustrated embodiment, vertebra 254 is misaligned with vertebra 252, indicative of a spondylolisthesis condition. It should be understood, however, that anchor extension 100 and installation instrument 20 have application in techniques which do not require or include correction of spondylolisthesis.

After engagement of screw portions 81 of anchors 80 to respective ones of the vertebrae 252, 254, anchor extension 30 is engaged to the anchor 80 engaged to vertebra 252 with set screw 96 partially threaded into yoke 88. Anchor extension 100 is manipulated to open jaws 164, 166 for positioning about arms 86 of yoke 88 of the anchor 80 engaged to vertebra 254. Anchor extension 100 is then manipulated to move second member 160 relative to first member 120 to the intermediate mounting configuration, where jaws 164, 166 are clamped along the outer surfaces of arms 86 of yoke 88 as discussed above.

Anchor extensions 30, 100 are then manipulated by pivoting yokes 88 to position anchor extensions 30, 100 adjacent one another so that pin 49 is received in receptacle 125 of second member 120. Inserter 24 is then secured to anchor extensions 30, 100 by placing one of the pins 60 in receptacle 132 of second member 120, and the other of pins 60 in the receptacle 48 of first anchor extension 30. Pins 60 are rotatably received in the adjacent ones of receptacle 48 and receptacle 132, and anchor extensions 30, 100 are secured to support arms 22 via clamping mechanism 21. Bores 51 and 168 of inner sleeve 50 and second member 160. respectively, remain substantially unobstructed for access to anchors 80 when installation instrument 20 is assembled.

Connecting element 90 is secured to distal arm 31 of inserter 24, and is advanced from a location outside the patient percutaneously to a location adjacent to anchors 80. In the illustrated embodiment shown in FIGS. 28-29, the distal or leading end portion of connecting element 90 is initially positioned between arms 86 of the anchor 80 engaged to anchor extension 30. The proximal or trailing end portion of connecting element 90 is positioned in the passage between jaws 164, 166 of second member 160 of anchor extension 100. Reducer members 140, 142 are positioned proximally of connecting element 90.

Connecting element 90 is then released from inserter 24. The leading end portion of connecting element 90 is secured to anchor 80 with a set screw 96 coupled to anchor extension 30. Distal arm 31 can be withdrawn from the patient, and inserter 24 uncoupled with anchor extensions 30, 100.

Figure 30:
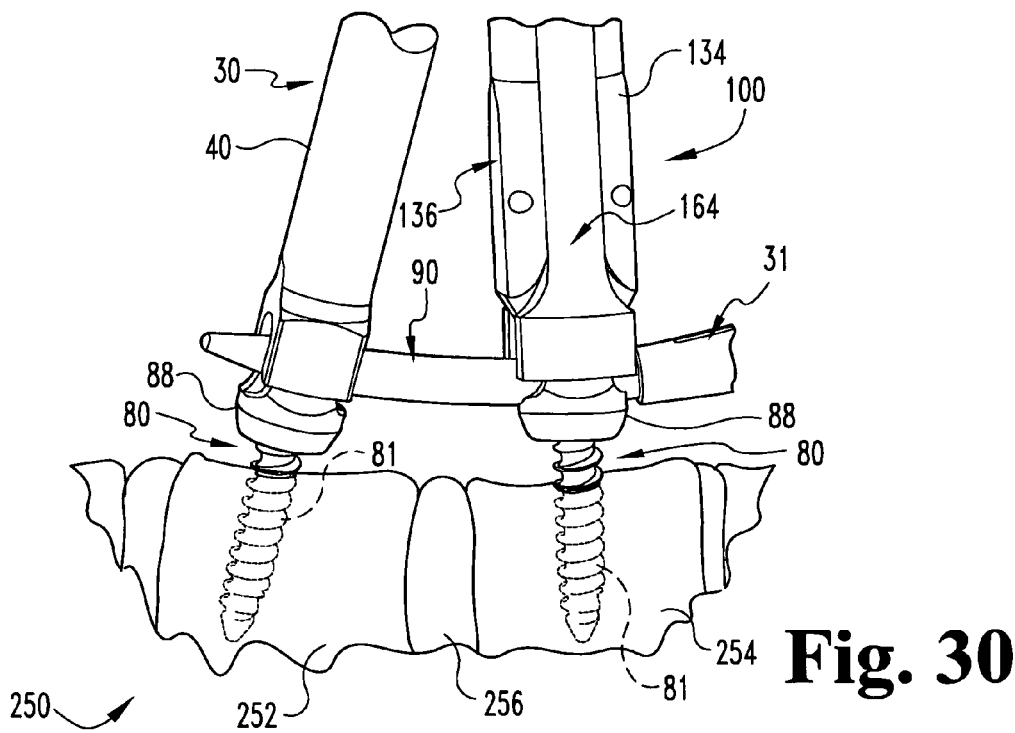
FIG. 30 is an elevation view of the distal portion of the installation instrument of FIG. 29 with the connecting element reduced into the head of the first anchor with the anchor extension of FIG. 7.

In FIG. 30, drive member 104 is then rotated to displace second member 160 proximally relative to first member 120, placing reducing members 140, 142 into contact with connecting element 90. Second member 160 is displaced relative to first member 120 toward the reducing configuration of anchor extension 100, displacing connecting element 90 transversely to its insertion axis and toward a position between arms 86 of the anchor 80 engaged to vertebra 254. In this reduced position, vertebra 254 is pulled into alignment with vertebra 252. A set screw 96 can then be advanced through passage 168 of second member 160 to secure connecting element 90 in anchor 80 of the reduced vertebra 254 to maintain vertebrae 252, 254 in their aligned position.

Drive member 104 is then rotated in the opposite direction to displace first and second members 120, 160 relative to one another to open jaws 164, 166 and release anchor 80 from therebetween. Anchor extensions 30, 100 are then withdrawn from the patient. Vertebrae 252, 254 can be fused or stabilized with one or more interbody devices in the disc space positioned through a second access portal, or through an access portal provided to accommodate one or both of the anchor extension 30, 100.

Referring to FIG. 31, there is shown anchor extension 100 with an alternate form of jaws 264, 266 coupled to second member 160. Jaw 264 includes a body 288 with guide slot 290 extending therealong. An anchor coupler 286 is located at a distal end of jaw 264. Similarly, jaw 266 includes a body 296 with guide slot 298 extending therealong. An anchor coupler member 294 is located at a distal end of jaw 264. Guide slots 290, 298 and anchor couplers 286, 294 can be configured identically to guide slots 190, 198 discussed above with respect to jaws 164, 166. Guide slots 290, 298 each include a proximal cammed portion to bias jaws 264, 266 away from another to facilitate engagement with anchor 80.

Body 288 includes a recessed portion 289 formed by a concavely curved surface that faces a recessed portion 297 formed by a concavely curved surface of body 296. The concavely curved surfaces of recessed portions 289, 297 are oriented toward one another to form a passage 299 therebetween that is larger than passage 95 formed between arms 86 of yoke 88. Passage 299 is also larger than the spacing between coupling members 286, 294 engaged with arms 86 of yoke 88. Passage 299 is structured to accommodate insertion of a connecting element with an enlarged portion, as discussed further below. Although passage 299 is shown with a circular shape, other shapes for passage 299 are also contemplated.

Figure 32:
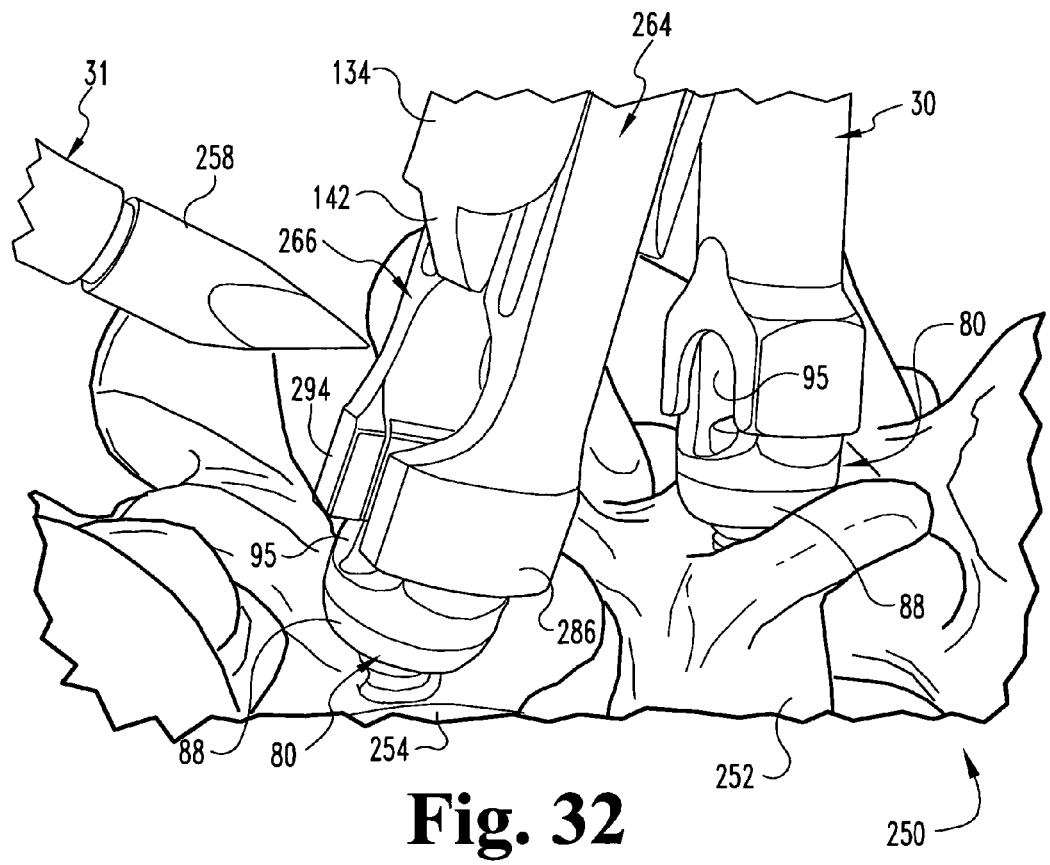
FIG. 32 is a perspective view of a spinal column segment with the anchor extension embodiment of FIG. 31 mounted to a first anchor, the anchor extension of FIG. 3 mounted to a second anchor, and a trocar positioned adjacent to the first anchor with the installation instrument of FIG. 1.
Figure 33:
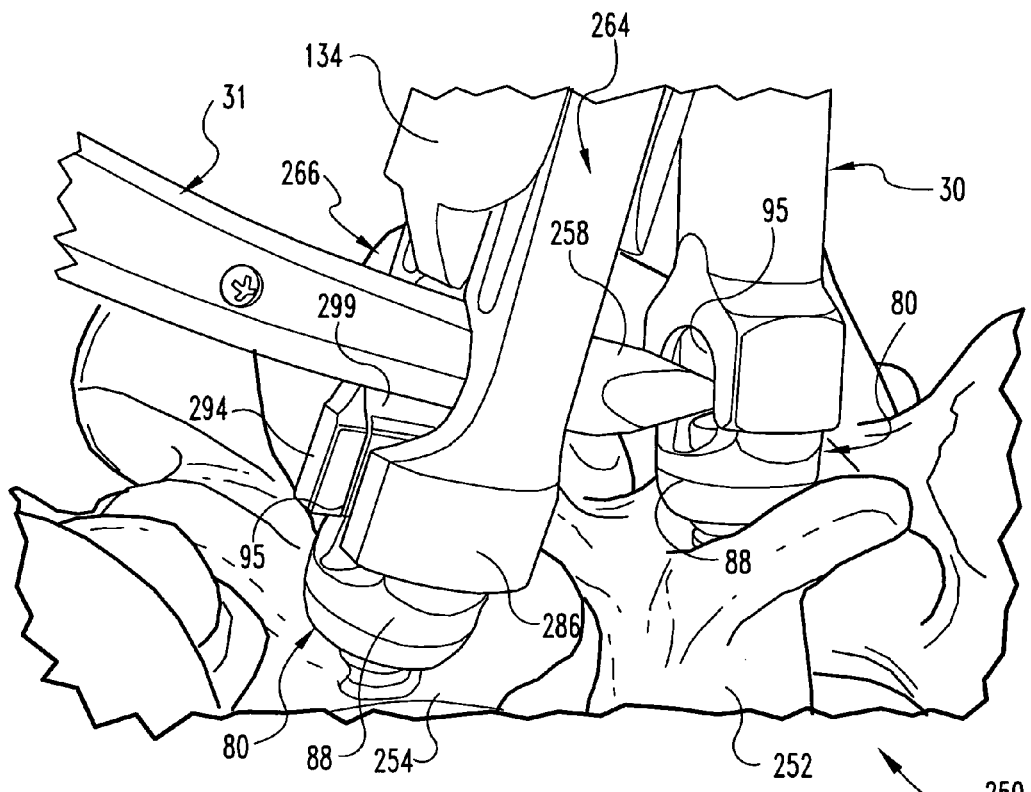
FIG. 33 is a perspective view of the spinal column segment, anchors and anchor extensions of FIG. 31 and FIG. 3 with the trocar positioned through the anchor extension embodiment of FIG. 31 and adjacent the passage of the second anchor.
Figure 34:
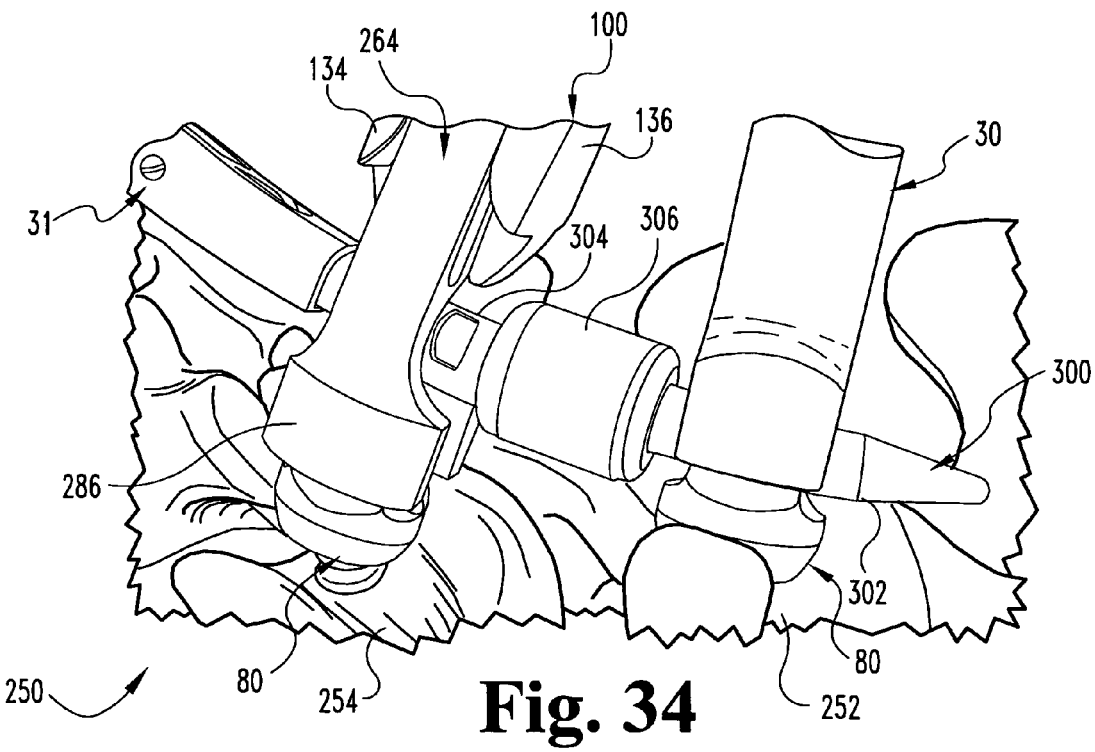
FIG. 34 is a perspective view of the spinal column segment, anchors, and anchor extensions of FIG. 32 with another embodiment connecting element positioned through the anchor extension of FIG. 31 and into the receiver of the second anchor.

In FIG. 32 anchors 80 are engaged to pedicles of adjacent vertebrae 252, 254 of spinal column segment 250. Anchor extension 30 is engaged to anchor 80 engaged to vertebra 252, and anchor extension 100 includes jaws 264, 266 coupled to the anchor 80 engaged to vertebra 254. Inserter 24 is mounted to anchor extensions 30, 100 with trocar 258 coupled to distal arm 31. Trocar 258 is inserted through passage 299 between jaws 264, 266 and also into passage 95 adjacent anchor extension 30. Trocar 258 forms an insertion path through the tissue to facilitate passage of a connecting element, such as connecting element 300 shown in FIG. 34.

Connecting element 300 includes a first end portion that is a distal leading end portion 302, a second end portion that is a proximal trailing end portion 304, and an intermediate portion 306. Intermediate portion 306 is flexible to allow relative movement between end portions 302, 304 to provide a desired stabilization characteristic. Connecting element 300 is inserted with inserter 24 such that first end portion 302 and intermediate portion 306 pass through passage 299. First end portion 302 is positioned into passage 95 of the anchor 80 engaged to anchor extension 30. Second end portion 304 is positioned between jaws 264, 266 adjacent passage 299, and intermediate portion 306 is positioned between anchor extensions 30, 100.

Figure 35:
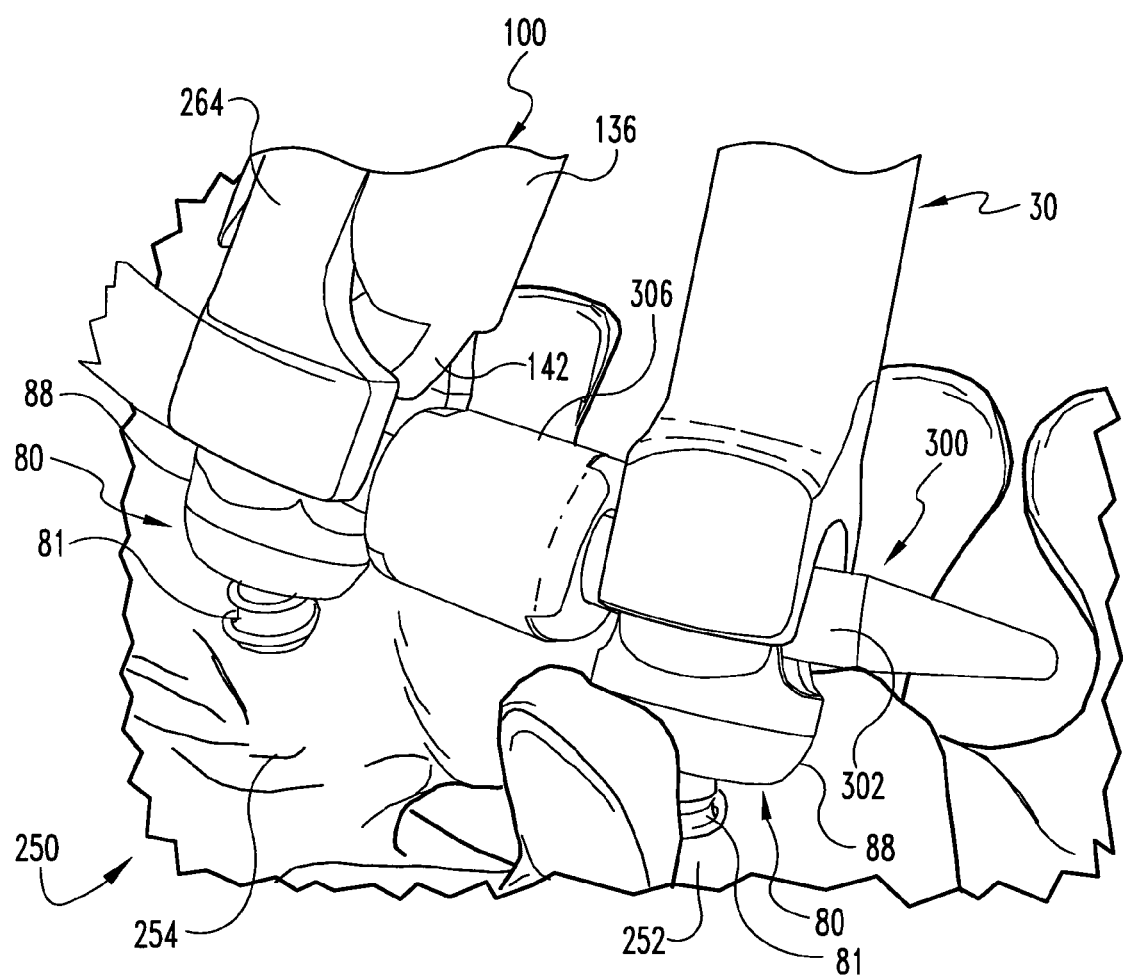
FIG. 35 is a perspective view of the spinal column segment of FIG. 34 with the connecting element embodiment of FIG. 34 reduced into the head of the first anchor with the anchor extension embodiment of FIG. 31.

First end portion 302 is engaged to the adjacent anchor 80 with set screw 96. As shown in FIG. 35, inner member 160 with alternate jaws 264, 266 is then moved relative to outer member 120 to reduce second end portion 304 of connecting element 300 into passageway 95 of the anchor 80 engaged to vertebra 254. Connecting element 300 can then be secured to the respective anchor 80 with set screw 96, as shown in FIG. 36. Connecting element 300 maintains a restored disc space height and/or alignment between adjacent vertebrae. In one form, connecting element 300 preserves motion between the adjacent vertebrae 252, 254.

Figure 37:
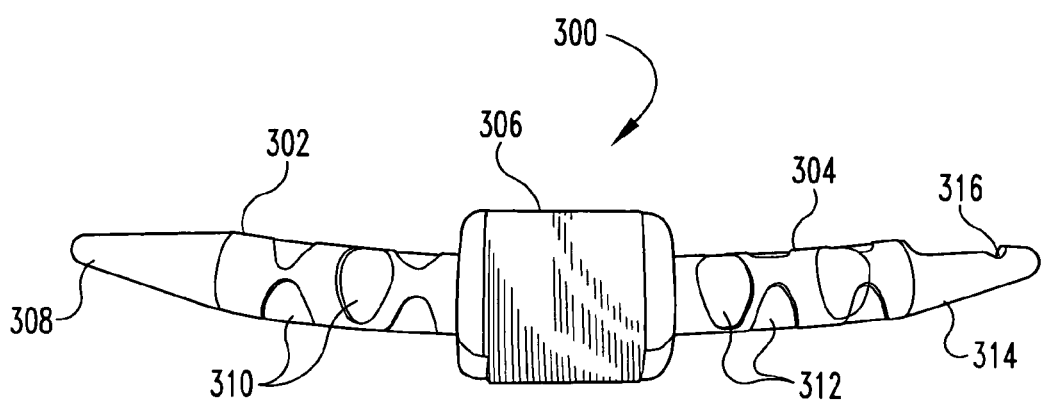
FIG. 37 is an elevation view of another embodiment connecting element.
Figure 38:
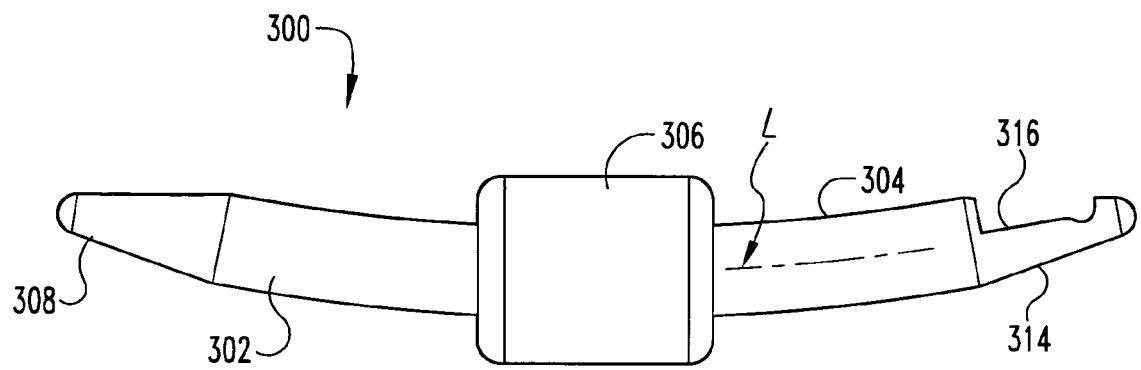
FIG. 38 is an elevation view of another embodiment connecting element.

Further discussion of connecting element 300 will be made with reference to FIGS. 37-42. In FIGS. 37-38, connecting element 300 includes intermediate portion 306 in the form of a flexible member that provides a shock absorbing effect in transmitting spinal column loads between the anchors to which it is engaged. Intermediate portion 306 can also permit relative movement between first and second end portions 302, 304 to allow motion of the spinal column segment to which connecting element 300 is engaged. In one embodiment, intermediate portion 306 provides connecting element 300 with a variable stiffness profile between anchors 80. In still further embodiments, intermediate portion 306 can be comprised of a resorbable material so that after a period of time the adjacent anchors are no longer linked to one another.

First end portion 302 of connecting element 300 includes a tapered leading end member 308 to provide a dilation effect and facilitate passage through skin and tissue in percutaneous insertion procedures. First end portion 302 may also include other configurations, including non-tapered configurations. Second end portion 304 can include an end member 314 with an indexed configuration 316 in the form of a notch for indexed engagement to inserter 24 to ensure that connecting element 300 is coupled in and maintained in the proper orientation relative to the inserter before and during percutaneous insertion. First end portion 302 and second end portion 304 can be substantially rigid to facilitate percutaneous insertion of connecting element 300 with inserter 24 and engagement with anchors 80. For example, first end portion 302 can dilate tissue to facilitate passage of intermediate portion 306 therethrough. Other embodiments contemplate that end member 314 is provided with other forms suitable for coupling with an inserter instrument. It is further contemplated that connecting element 300 can be inserted manually or with instruments other than inserter 24.

Connecting element 300 is curved along radius R to facilitate insertion along an arced insertion path with inserter 24. Other configurations for connecting element 300 are contemplated, including configurations discussed above for connecting element 90. As shown in FIG. 37, one or both of the first and second end portions 302, 304 can include a number of pits 310, 312, respectively, to provide increased frictional engagement with the set screw 96 and anchor 80 to which the end portion 302, 304 is engaged. Smooth surface profiles for one or both of end portions 302, 304, such as shown in FIG. 38, are also contemplated.

Figure 39:
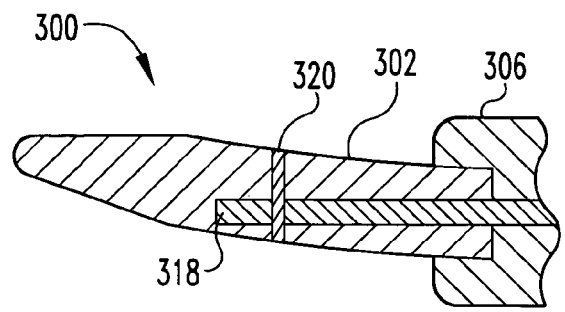
FIG. 39 is a sectional view of a distal end portion of another embodiment connecting element.

Various embodiments of connecting element 300 contemplate various techniques for securing first and second portions 302, 304 to intermediate portion 306. In FIGS. 39-42, such alternate embodiments are described with reference to first end portion 302, it being understood the second end portion 304 can be similarly configured for securement with intermediate portion 306. In FIG. 39 there is shown first end portion 302 and intermediate portion 306 with aligned passages for receiving a coupling member 318 therethrough. Coupling member 318 can be, for example, a rigid rod or wire secured by crimping end portions 302, 304 thereagainst. Additionally or alternatively, a pin 320 can be provided that extends transversely through coupling member 318 and into end portions 302, 304. Coupling member 318 links the distal and proximal portions to one another to maintain intermediate portion 306 therebetween. End portions 302, 304 can move relative to one another in response to flexing of intermediate portion 306. Coupling member 318 can be bendable to facilitate this relative movement.

Figure 40:
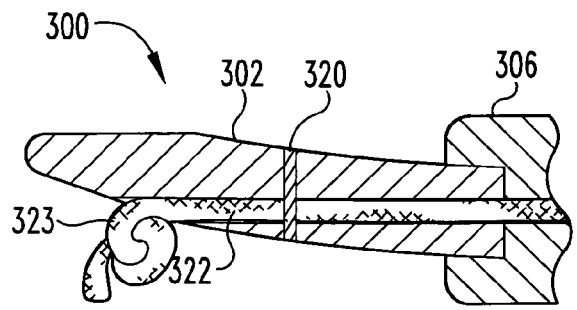
FIG. 40 is a sectional view of a distal end portion of another embodiment connecting element.

In FIG. 40 there is shown another embodiment coupling member in the form of a tether 322 extending through the aligned passages in end portions 302, 304 and intermediate portion 306. Tether 322 includes a stop member 323, illustrated in the form of a knot providing an enlarged end sized to prevent entry into the passage through end portion 302. Other forms for enlarged end 323 are also contemplated, including a swage, ball, or other enlarged device or form at the ends of the passages to secure first end portion 302 and second end portion 304 to intermediate portion 306. In a further form, a pin 320 can be provided that extends through and intersects tether 322 to secure it to respective ones of the end portions 302, 304.

Figure 41:
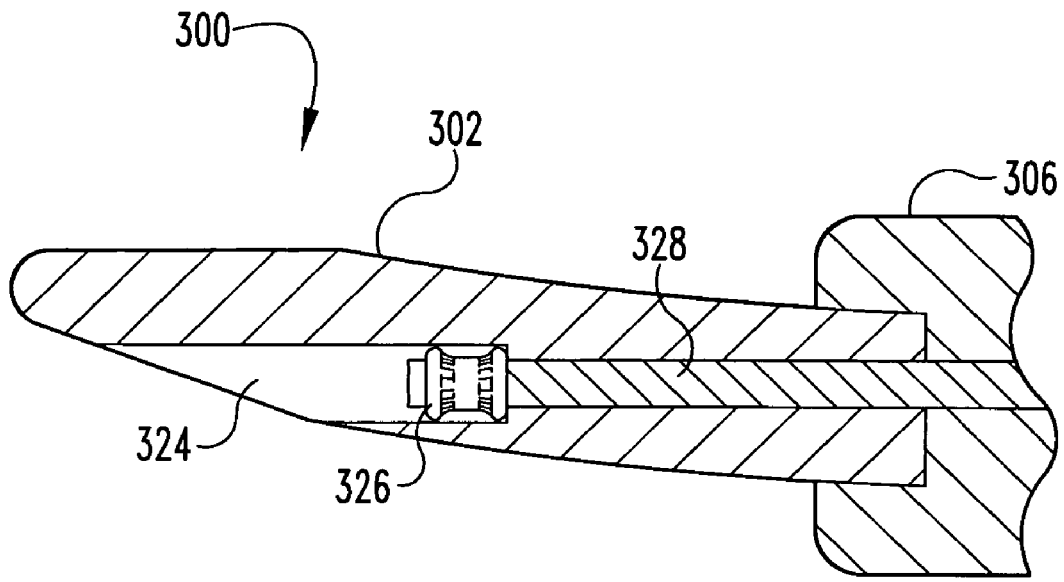
FIG. 41 is a sectional view of a distal end portion of another embodiment connecting element.

In FIG. 41 there is shown another embodiment coupling member designated as 328 which extends through intermediate portion 306 and links end portions 302, 304 thereto. A stop member 326 is received in an enlarged passage portion 324 to provide an enlarged end that secures coupling member 328 to first end portion 302, it being understood that proximal portion 304 can be similarly arranged. Stop member 326 can axially float or move in passage portion 324 in response to compression loads applied to intermediate portion 306, allowing end portions 302, 304 to move relative to one another. Enlarged passage portion 324 further recesses the stop member 326 so that it does not extend or project outwardly from first end portion 302.

Figure 42:
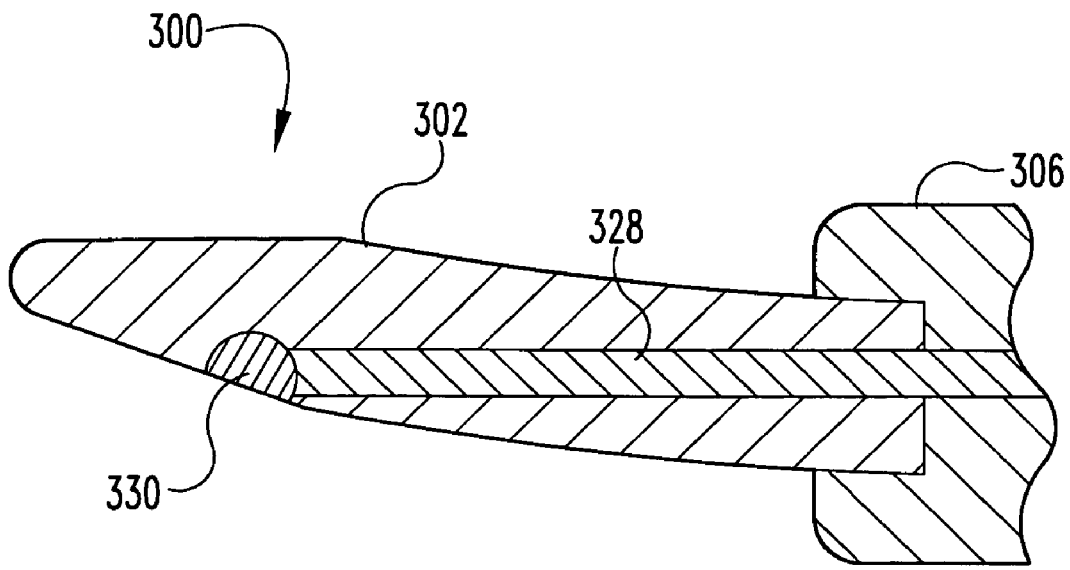
FIG. 42 is a sectional view of a distal end portion of another embodiment connecting element.

In FIG. 42, coupling member 328 is axially secured to end portions 302, 304 with a stop member 330. Stop member 330 can be in the form of a ball or material fragment that is larger than the passage through which coupling member 328 extends. Stop member 330 is recessed in first end portion 302 so that it does not protrude therefrom.

Figure 43:
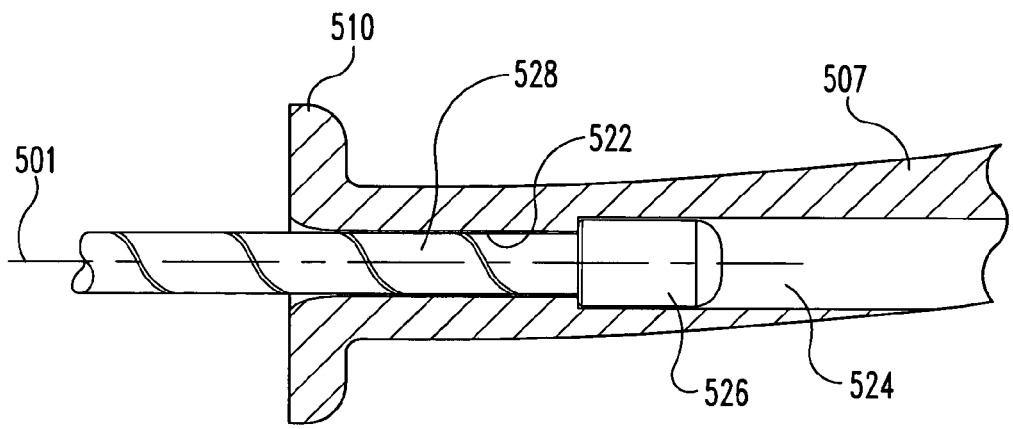
FIG. 43 is a sectional view of part of an end portion of another embodiment connecting element.
Figure 44:
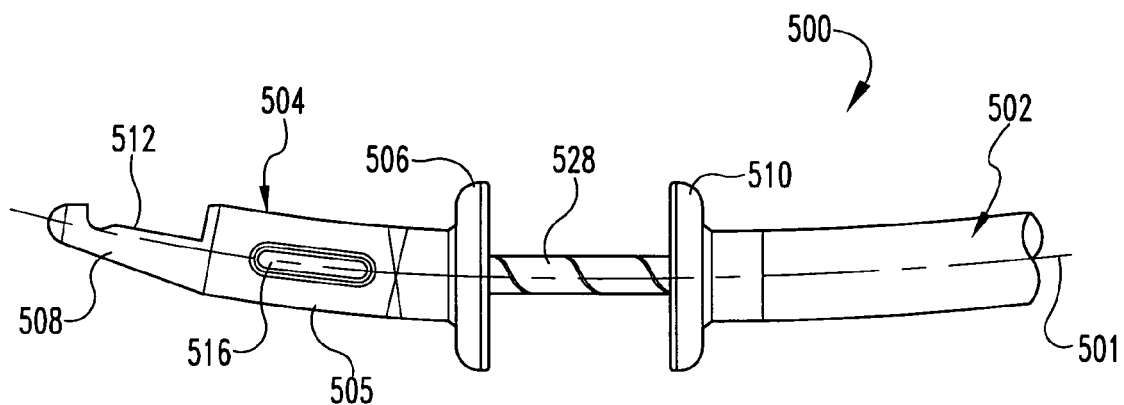
FIG. 44 is an elevation view showing the part of the connecting element of FIG. 43 with the other end portion.
Figure 45:
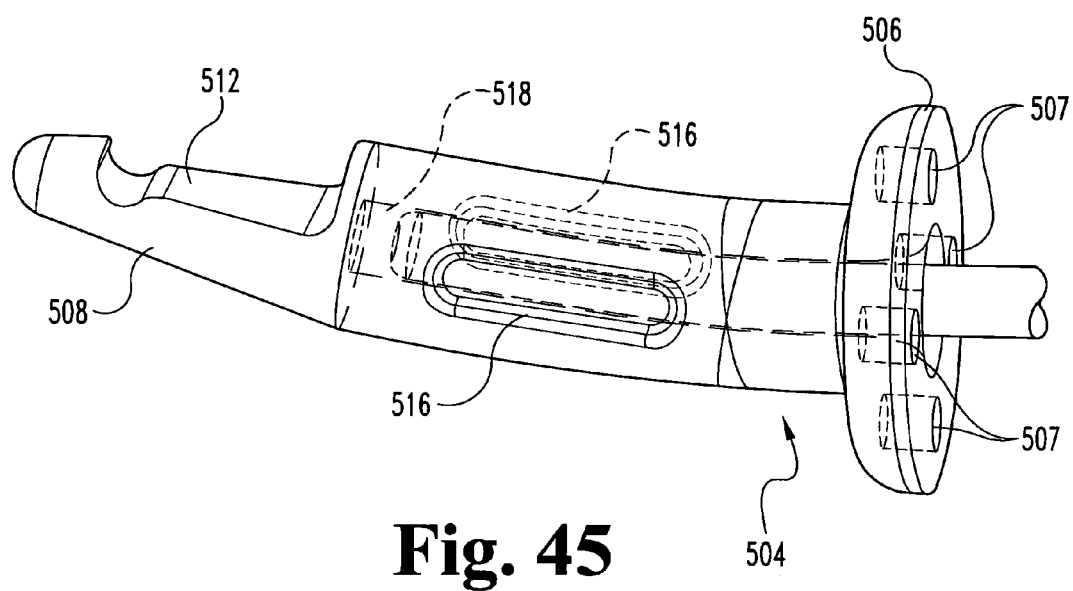
FIG. 45 is a perspective view of the other end portion of the connecting element of FIG. 44.
Figure 46:
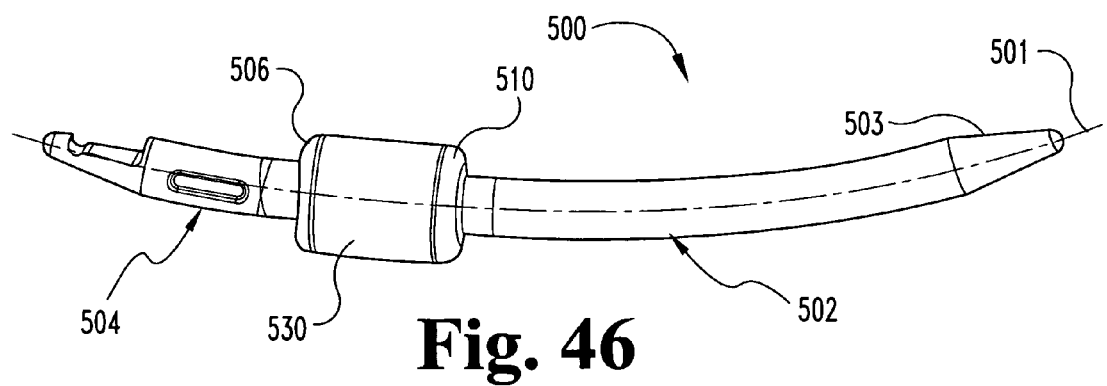
FIG. 46 is a perspective view of one embodiment connecting element including the end portions of FIGS. 43-45.
Figure 47:
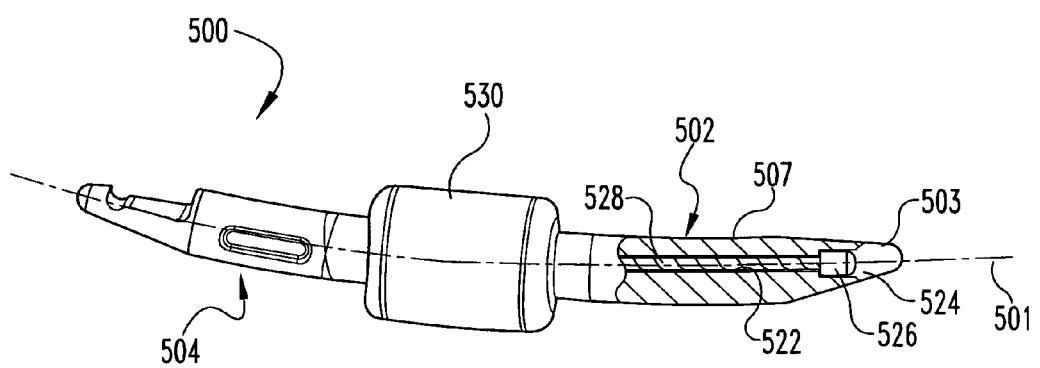
FIG. 47 is a perspective view in partial section of another embodiment connecting element.

Another embodiment connecting element 500 is shown in FIGS. 43-45. In FIG. 43, only a part of a first end portion 502 is shown, and in FIG. 44 there is shown a part of first end portion 502 and a second end portion 504 spaced therefrom to accommodate a flexible intermediate portion 530 therebetween, as shown in FIGS. 46 and 47. A coupling member 528 extends between and flexibly links first and second end portions 502, 504.

First end portion 502 includes a flange 510 extending thereabout at one end of a rod-like body 507 and a tapered end member 503 at the opposite end. End member 502 can facilitate percutaneous introduction and passage of connecting element 500 through skin and tissue relative to one or more anchors in a minimally invasive procedure. A first passage 522 extends axially along at least a portion of the length of first end portion 502. First passage 522 opens centrally at flange 510.

Second end portion 504 includes a flange 506 at one end of a rod-like body 505, and a tapered end member 508 at the opposite end of body 505. A second passage 518 extends along at least a portion of the length of second end portion 504, and opens centrally at flange 506. As discussed further below, intermediate flexible portion 530 can be positioned between and engaged to flanges 506, 510. Tapered end member 508 can included a recess forming an indexed configuration 512 to facilitate engagement with an insertion instrument in a desired orientation relative thereto. Second end portion 504 further includes exterior crimping recesses 516 in body 505 along second passage 518 to facilitate receipt of and crimping of body 505 by a crimping instrument (not shown.)

The rod-like bodies of the end portions 502, 504 can include a circular cross-section transversely to longitudinal axis 501. Intermediate portion 530 can include a cylindrical body having a circular cross-section transverse to longitudinal axis 501 that is enlarged relative to the cross-sections of end portions 502, 504.

Coupling member 528 extends into first and second passages 522, 518 and can be engaged to second end portion 504 by crimping the sides of body 505 at recesses 516. The crimping force collapses body 505 to grip coupling member 528 in passage 518 extending through body 505. In one embodiment, coupling member 528 is a metal cable, and body 505 is collapsed by crimping to frictionally and mechanically engage the cable to body 505 in passage 518. Coupling member 528 could also be engaged to first end portion 502 in a similar manner, or in any other manner discussed herein. Other coupling members are also contemplated, including those made from non-metal tethers, solid metal rods, and material with super memory properties such as Nitinol and shape memory polymers.

Flanges 506, 510 can be adapted to engage flexible intermediate portion 530 therebetween. In one embodiment, flanges 506, 510 include holes, such as holes 507 shown with respect to flange 506, to receive attachment means such as fasteners, sutures, threads, wires, or other devices to engage intermediate portion 530 to the respective flange. In another embodiment, intermediate portion 530 is injection molded between flanges 506, 510. The injected material can flow into holes 507 in the flanges in order to form around coupling member 528 and at least partially around the flanges to provide engagement therewith. In still another embodiment, intermediate portion 530 is molded over flanges 506, 510. In any embodiment, connecting element 500 can be provided with or without coupling member 528, and with or without holes in flanges 506, 510.

For embodiments including coupling member 528, it extends from second portion 504 through intermediate portion 530 and into second passage 522 of first end portion 502. In the illustrated embodiment of FIG. 43, a stop member 526 is received in an enlarged passage portion 524 of first passage 522 to provide an abutment structure that secures coupling member 528 to end portion 502. Stop member 526 can axially float or move in passage portion 524 away from intermediate portion 530 in response to compression loads applied to connecting element 500. The floating capability of stop member 526 allows end portions 502, 504 to move toward one another and minimize the potential for buckling of coupling member 528 in intermediate member 530 in response to axial compression loads from the spinal column. The floating stop member 526 allows reduction of the overall length of the connecting element 500 in response to compression of the intermediate portion while preventing an assembled connecting element 500 from coming apart in response to tension or torsional loading. In one embodiment, stop member 526 is a ferrule that is crimped or rotary swaged onto the end of a cable comprising coupling member 528. Other embodiments contemplate other coupling arrangements as discussed herein.

In the FIG. 43 embodiment, first end portion 502 includes body 507 extending along a longitudinal axis 501. Longitudinal axis 501 and body 507 are curved in the illustrated embodiment, and first passage 522 extends linearly along first end portion 502 such that it diverges from longitudinal axis 501 in the direction away from second end portion 504 and opens along a sidewall of body 507. Other embodiments contemplate other configurations for passage 522. For example, FIG. 47 shows passage 522 extending along longitudinal axis 501 to end member 503. An enlarged passage portion 524 is formed in end member 503 in communication with passage 522, and receives stop member 526 therein. Stop member 526 is axially movable in passage portion 524 to facilitate compression of intermediate portion 530 and movement of end portion 502, 502 relative to one another. Placement of the opening of passage 524 at end member 503 cam prevent the anchor to which connecting element 500 is engaged from interfering with movement of stop member 526.

Figure 48:
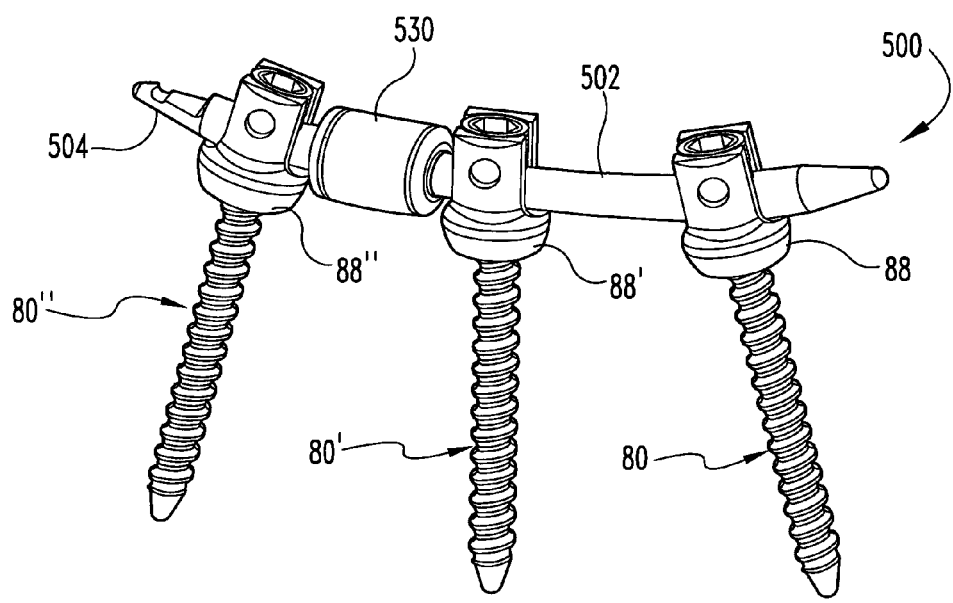
FIG. 48 is a perspective view of the connecting element of FIG. 46 secured to anchors.

Connecting element 500 can be configured to extend between adjacent vertebrae for a single level stabilization procedure, or a multi-level stabilization procedure as shown in FIG. 46. In FIG. 46 there is shown connecting element 500 with first and second end portions 502, 504 and an intermediate portion 510 between flanges 506, 510. Connecting element 500 extends along longitudinal axis 501. First end portion 502 includes a length along longitudinal axis 501 that is greater than the length of second end portion 504 along longitudinal axis 501. As shown in FIG. 48, connecting element 500 can extend between three anchors engaged to respective ones of three vertebrae for a two level stabilization procedure. For example, intermediate portion 530 is positioned between an outer anchor 80" and an intermediate anchor 80', and second end portion 504 is engaged to outer anchor 80". First end portion 502 extends between and is engaged to intermediate anchor 80' and an outer anchor 80.

In one procedure, anchor 80 is engageable to a first vertebra, anchor 80' is engageable to a second vertebra, and anchor 80" is engageable to a third vertebra. When so engaged, intermediate portion 530 allows the vertebrae to which anchors 80', 80" are engaged to move or flex relative to one another, but limits extension and flexion motion to provide a stabilizing effect. First end portion 502 is engaged to intermediate anchor 80' and also to first outer anchor 80. When so engaged, the vertebrae to which anchors 80', 80 are engaged are rigidly coupled to one another to prevent relative movement therebetween.

Connecting element 500 can be guided into position between the anchors using an installation instrument as discussed above. The installation instrument may include extenders extending from any one, two or three of the anchors. Other techniques contemplate insertion with an open surgical technique, or guiding of the connecting element distally along extenders extending proximally from one or more of the anchors. Connecting element 500 can be employed in fusion procedures or in procedures employing dynamic stabilization without fusion. In fusion procedures, fusion promoting material and/or one or more fusion devices, implants, or bone graft are placed in the disc space between adjacent vertebrae. In such procedures, a single level connecting element may be coupled between the vertebrae if dynamic stabilization is desired. If rigid stabilization is desired, a connecting element with an elongated end portion can be provided and engaged between the vertebrae to be fused, and one or more adjacent vertebral levels can be dynamically stabilized with the intermediate portion 530 engaged between these or more other vertebral levels.

While in the illustrated embodiments the connecting elements are shown as being adapted to extend along one or two vertebral levels, the connecting elements can also extend along three or more vertebral levels. For example, one of the end portions 502, 504 can include a length that extends along multiple vertebral levels to be fused to provide rigid stabilization of these levels, while the other of the end portions 502, 504 includes a length adapted to extend along at least one vertebral level to provide a flexible intermediate portion 530 between vertebrae for dynamic stabilization.

Figure 50:
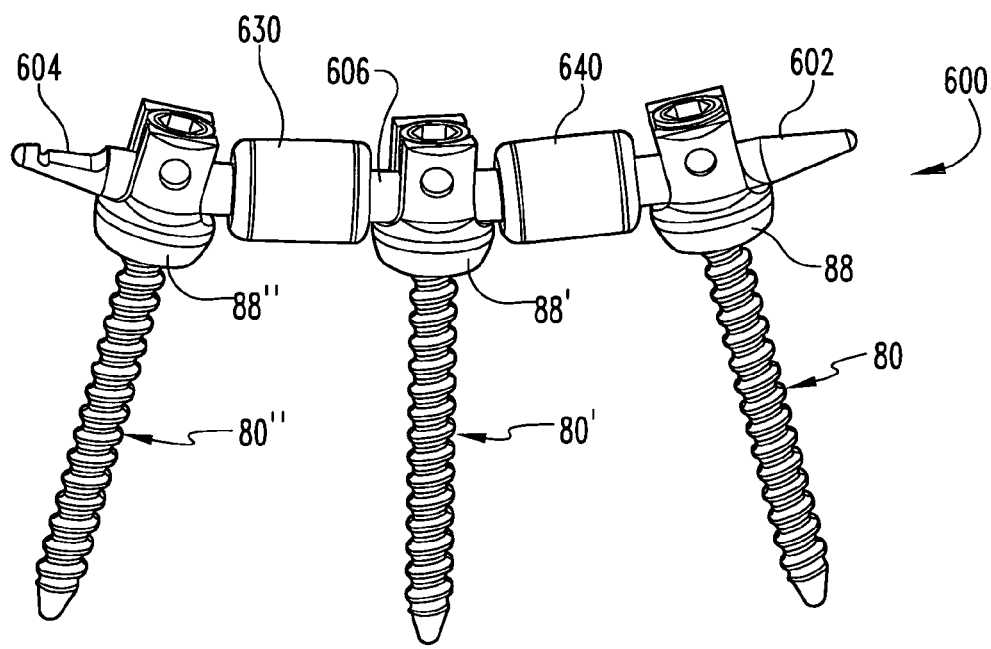
FIG. 50 is a perspective view of the connecting element of FIG. 49 secured to anchors.
Figure 49:
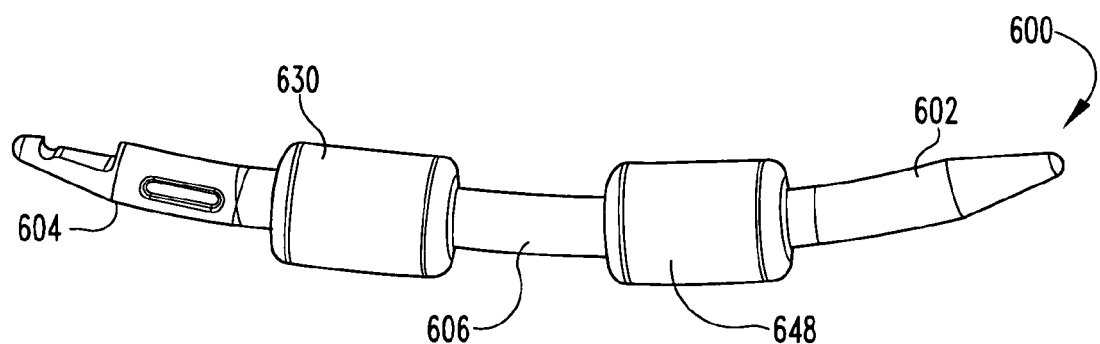
FIG. 49 is a perspective view of another embodiment connecting element.

In a further embodiment shown in FIGS. 49 and 50, a connecting element 600 is provided with a first end portion 602, a second end portion 604, and a linking portion 606 therebetween. A first flexible intermediate member 630 is provided between second end portion 604 and linking portion 606, and a second flexible intermediate member 640 is provided between linking portion 606 and first end portion 602. As shown in FIG. 50, when engaged to three vertebrae for a two level stabilization procedure, a flexible intermediate portion extends between each of the paired anchors 80, 80' and anchors 80', 80" for dynamic stabilization of each vertebral level.

Linking portion 606 and/or end portions 602, 604 can include flanges at opposite ends thereof to which intermediate portions 630, 648 are engaged, and can include any other type of connection or coupling arrangement as discussed above with respect to connecting elements 300, 500. In a further embodiment of connecting element 600, linking portion 606 has a length adapted to extend along one or more vertebral levels, and is engaged to anchors secured to vertebrae at each of the corresponding vertebral levels. This embodiment allows dynamic stabilization of the vertebral levels located both cephaladly and caudally of the one or more vertebral levels to be fused and/or rigidly stabilized by linking portion 606.

The coupling member embodiments discussed herein can be in the form of a rod, tether, cable, wire, suture, or other suitable form and can be made from resorbable or non-resorbable material, such as polyethylene, stainless steel, and titanium, for example. Still other embodiments contemplate one or more intermediate portions mechanically attached, chemically or mechanically bonded to the respective end portions and/or linking portions without a coupling member extending through the assembly. For example, the intermediate portion can be molded, fused, adhered, riveted, other otherwise attached to respective ones of the end portions and/or linking portions.

The flexible intermediate portions discussed herein can be made from any suitable material allowing at some motion of the vertebral level along which the intermediate portion is engaged. For example, the intermediate portions can be made from elastomers, polycarbonateurethane, polyetheretherketone, or other polymer material. The intermediate portions can be made from resorbable material. In still another form, the intermediate portions include springs, which can be made from metal or other suitable material.

It is further contemplated that the intermediate portions can be provided with a varying stiffness profiles to vary the stiffness properties of the connecting element and control movement of the one or more dynamically stabilized vertebral levels. Such varying stiffness profiles can be provided across the cross-section of a single flexible intermediate portion of a particular connecting element, or provided between different intermediate portions of a single multi-level connecting element, or provided between a number of connecting elements in a kit where the connecting elements includes one or more intermediate portions with a stiffness profile that varies relative to one or more of the intermediate portions of the other connecting elements.

In one embodiment, the hardness characteristics of the material comprising the flexible intermediate portion is varied. For example, the durometer of an elastomer material comprising the one or more flexible intermediate portions may vary to allow selection and implantation of a connecting element providing the desired motion characteristics for the vertebral level.

In another embodiment, the connecting element is provided with a coupling member the couples the first and second end portions to one another through the flexible intermediate portion. The diameter of the coupling member can be varied so that the connecting elements with flexible intermediate portions extending about a coupling member with a greater diameter are stiffer than connecting elements with a flexible intermediate portion extending about a coupling member of lesser diameter.

In a further embodiment, the coupling member can be pre-tensioned so that the end portions are compressed against the flexible intermediate portion when engaged thereto. The amount of pre-tension can range from 0 to the tensile break strength of the coupling member. The greater pre-tension loading of the coupling member results in stiffer flexible intermediate portion behavior since the preloading compresses the flexible intermediate portion between the end portions.

In still a further embodiment, the length of intermediate portion can be varied. For example, as shown in FIG. 51, connecting element 700 includes an intermediate portion 706 having a length L between the respective end portions 702, 704. The length L can be varied between intermediate portions of the same or differing connecting elements to vary stiffness profiles. The intermediate portion having the greater length L will be less stiff than intermediate portions with a smaller length L. In one particular example, the range of lengths L can range from 6 millimeters to 15 millimeters or more as measured out-to-out of the flanges 708, 710 engaged to the intermediate portion.

In another embodiment connecting element, the flexible intermediate member can include a reduced cross-sectional area to vary the stiffness profile. For example, FIGS. 52A-52B shown a flexible intermediate portion 730 having a central passage 732 for receiving a coupling member, although omission of passage 732 is also contemplated. A number of bores 734 are provided axially through the body of intermediate portion 730 to reduce its cross-sectional area and thus reduce its stiffness. In one embodiment, bores 734 can be concentrated or provided in greater proportion along one side of intermediate portion 730 to provide a varying stiffness profile across the cross-section of intermediate portion 730. For example, the concentrated bores can be oriented adjacent the vertebrae in a posterior stabilization procedure. Extension motion between the vertebrae would be met with greater resistance by the side of intermediate portion 730 with the greater cross-sectional area being more resistant to compression loading resulting from the extension motion. Flexion motion between the vertebrae would be provided less resistance due to the side of intermediate portion 730 having a lesser cross-section area being positioned adjacent the vertebrae and being more easily compressed to allow greater flexion motion.

In still another embodiment connecting element, the flexible intermediate member 740 in FIGS. 53A-53B show a flexible intermediate portion 740 having a central passage 742 for receiving a coupling member, although omission of passage 742 is also contemplated. A number of bores 744 are provided transversely to the longitudinal axis through the body of intermediate portion 740 to reduce its cross-sectional area and thus reduce its stiffness. In one embodiment, bores 744 can be concentrated along one side of intermediate portion 740 to provide a varying stiffness profile across the cross-section of intermediate portion 740. For example, the side of intermediate portion 740 with the concentrated or greater proportion of bores 744 can be oriented adjacent the vertebrae in a posterior stabilization procedure, providing greater resistance to extension motion between the vertebrae than flexion motion between the vertebrae.

Figure 54:
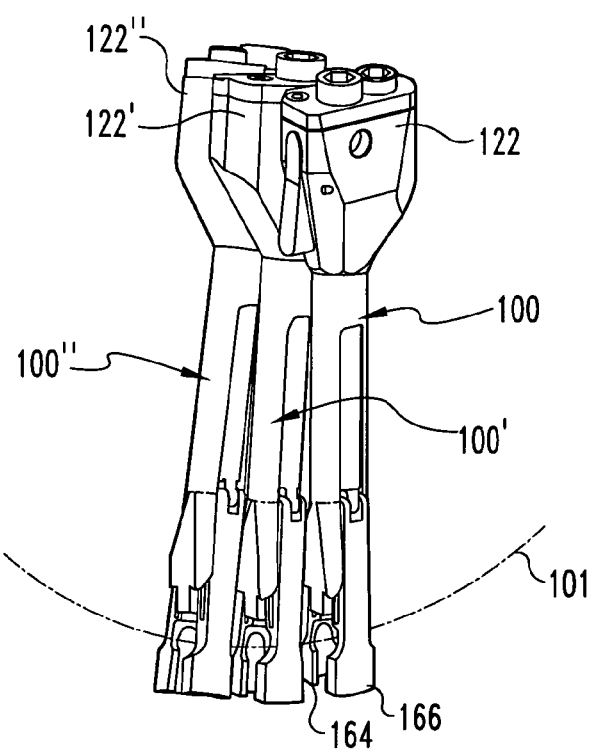
FIG. 54 is a perspective view of one embodiment set of anchor extensions mountable to anchors engaged to vertebrae in a multi-level stabilization procedure.

Referring now to FIG. 54, there is shown three anchor extensions 100, 100', 100" which can be configured substantially identically to one another. Anchor extensions 100, 100', 100" are removably engageable to respective ones of anchors 80, 80', 80", which are engageable to respective ones of three vertebrae. The anchor extensions include jaws 164, 166 movable relative to one another to releasably engage the respective anchor therebetween. The anchor extensions are movable relative one another by pivoting the respective receiver of the anchor to which the anchor extension is engaged, allowing the positioning of proximal housing portions 122, 122', 122" adjacent one another. The respective receivers of anchor 80, 80', 80" are aligned so that their respective passages are aligned along an insertion axis 101. Housing portion 122' can be positioned between and coupled to housing portions 122, 122" to maintain its orientation therebetween. Other embodiments contemplate that one or more of the anchor extensions 100 have another form, such as that shown for anchor extension 30.

Figure 55:
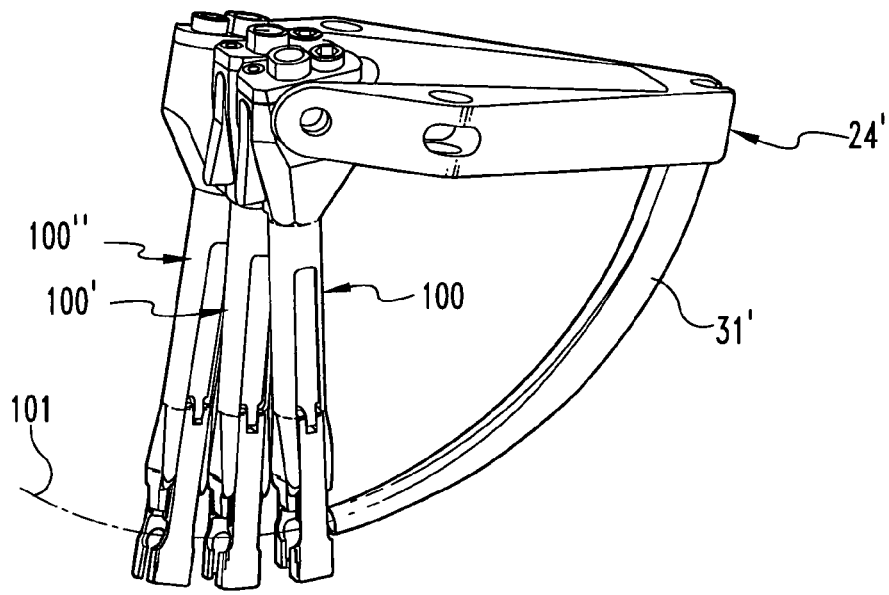
FIG. 55 is a perspective view of an inserter instrument for minimally invasive insertion of a multi-level connecting element mounted to the anchor extension of FIG. 54.

In FIG. 55 an inserter 24' is coupled to anchor extensions 100, 100', 100". Inserter 24' can be substantially identical to inserter 24 discussed above except it is sized to accommodate at least three anchor extensions 100, 100', 100" therebetween. Inserter 24' includes an arm 31' movable along insertion axis 101 by pivoting inserter 24' about the proximal ends of anchor extensions 100, 100". Any of the multi-level connecting element embodiments discussed above can be releasably coupled to inserter 24', and guided from a location remote from the anchors 80, 80', 80" to a position where the connecting element extends between anchors 80, 80" 80". Any one or all of the anchor extensions 100, 100', 100" may include arms configured with a passage to accommodate an enlarged intermediate portion of the connecting element, such as shown in FIG. 31. After positioning of the connecting element adjacent the receivers of the anchors, any one or combination of anchor extensions 100, 100', 100" can be manipulated to reduce displacement between the vertebrae and/or to reduce the connecting element into position in the respective receivers of the anchors 80, 80', 80".

In one embodiment, insertion axis 101 is a percutaneous path that extends from a location at the skin of the patient through the anchors 100, 100' 100". In another embodiment, insertion axis 101 extends between anchor extensions 100, 100', 100" from the anchors to the skin. The connecting element is guided between the anchor extensions through an incision at the skin level and along the anchor extensions to the anchors. Other embodiments contemplate placement of the connecting element with other minimally invasive and open surgical techniques.

Figure 56:
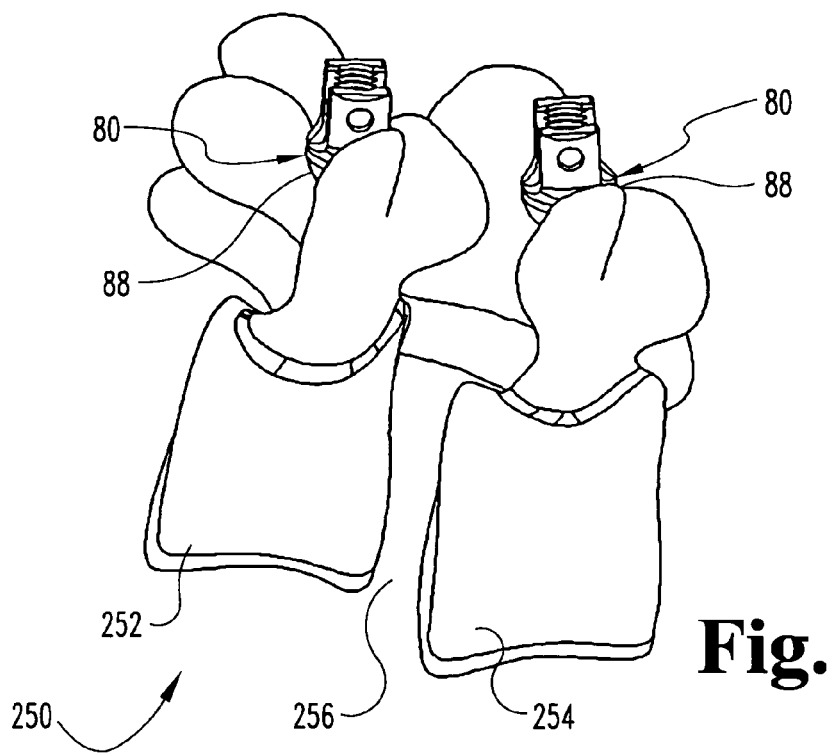
FIG. 56 is a spinal column segment with anchors secured to pedicles of adjacent vertebrae in spondylolisthesis.

Referring now to FIGS. 56-61 there is shown spinal column segment 250 with first vertebra 252 and second vertebra 254. Disc space 256 is between vertebra 252, 254. In FIG. 56 spinal column segment 250 is shown with grade 1 spondylolisthesis, where vertebra 254 is the L4 vertebra and vertebra 252 is the L5 vertebra. An anchor 80 is secured to the pedicles of each of the vertebra 252, 254. It is contemplated that anchor extensions, such as anchor extensions 30, 100 discussed above, could be attached to respective ones of the anchors 80 before anchors 80 are inserted and secured to the vertebrae. It is further contemplated that anchors 80 can be secured to the adjacent vertebrae, and then anchor extensions 30, 100 attached to respective ones of the anchors 80. Anchor extension 30 can be provided in any form suitable to engage anchor 80 secured to vertebra 252 and extend percutaneously therefrom to a location outside the patient's body. Also contemplated are multi-level stabilization procedures using anchor extensions and instruments such as shown in FIGS. 54-55.

Figure 57:
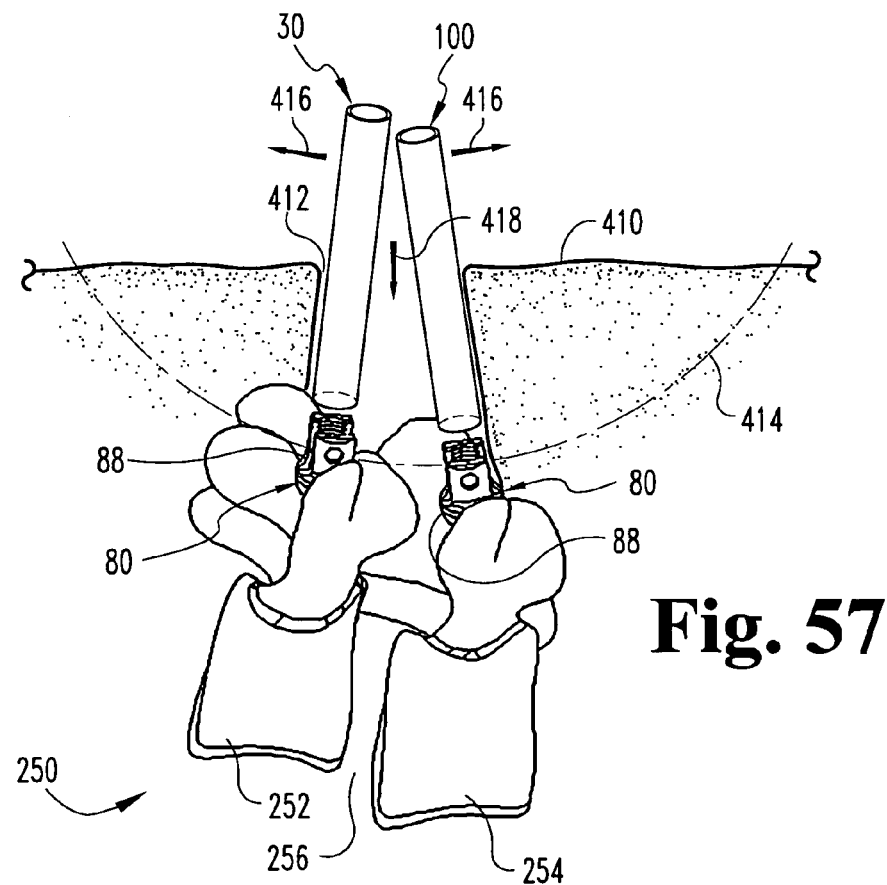
FIG. 57 is the spinal column segment of FIG. 56 with anchor extensions shown diagrammatically adjacent corresponding ones of the anchors and in exploded view therefrom for clarity.

In FIG. 57 anchor extensions 30, 100 are shown diagrammatically adjacent corresponding ones of the anchors and in exploded view therefrom for clarity. When anchors 80 include pivotal receivers or yokes 88, anchor extensions 30, 100 can be manipulated through the skin and tissue to align the passages of yokes 88 to receive connecting element 400. Connecting element 400 can be configured like any of the connecting element embodiments discussed herein, including those for single level and multi-level stabilization. The connecting element can provide rigid stabilization, flexible stabilization or combinations thereof at various vertebral levels.

In one embodiment, connecting element 400 includes a curved body 404 extending between a leading tapered end 402 and a trailing end 406. Trailing end 406 includes an indexed recess 408 for coupling with distal arm 31' of inserter 24 as discussed above. Anchor extensions 30, 100 can be coupled together at their proximal ends and mounted with an inserter, such as inserter 24. Inserter 24 guides insertion of connecting element 400 along a percutaneous insertion path 414 aligned with the at least the passages of yoke of the anchor 80 secured to vertebra 252. In a further embodiment, an inserter type instrument can be coupled to only of the anchor extensions 30, 100 to percutaneously guide the connecting element to a location adjacent the anchors.

Alternatively, connecting element 400 can be percutaneously inserted through an incision 412 in the skin and tissue 410 between anchor extensions 30, 100. Connecting element 400 can be held with forceps or other suitable insertion instrument, such as described in U.S. Pat. No. 10/202,918 filed Jul. 25, 2002, which is incorporated herein by reference. In such a procedure, connecting element 400 could be provided without a tapered leading end or indexed trailing end. Furthermore, the inserter is not mounted to one or both of the anchor extensions 30, 100 during insertion of the connecting element.

Figure 58:
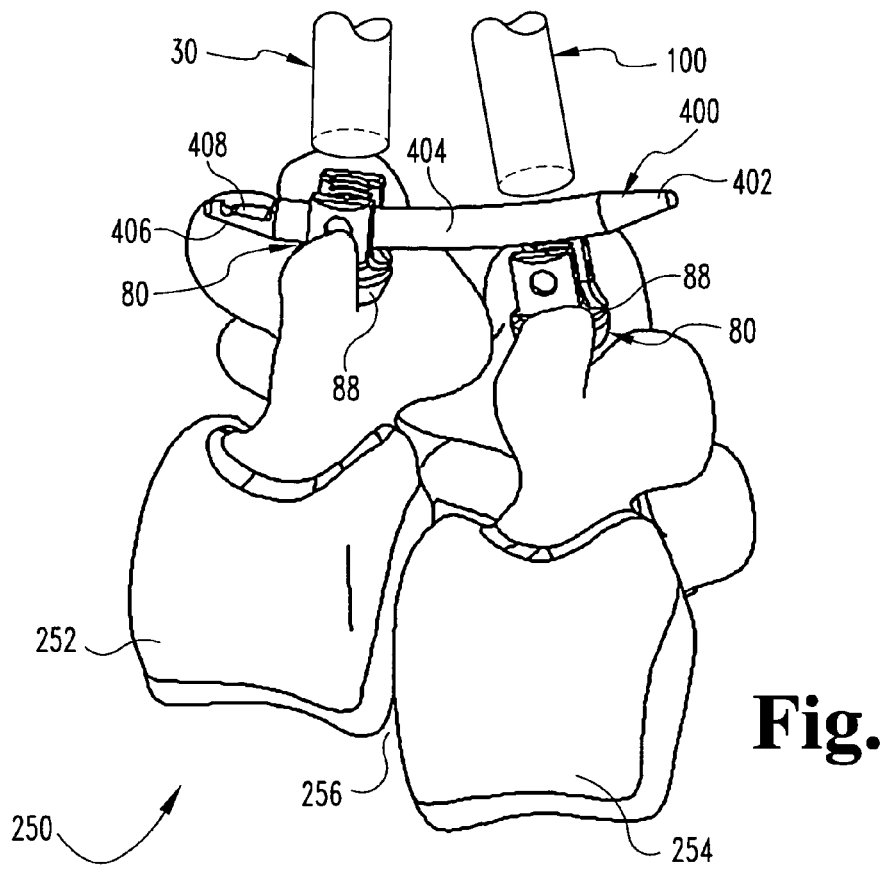
FIG. 58 is the spinal column segment of FIG. 57 with a connecting element positioned between the anchors.
Figure 59:
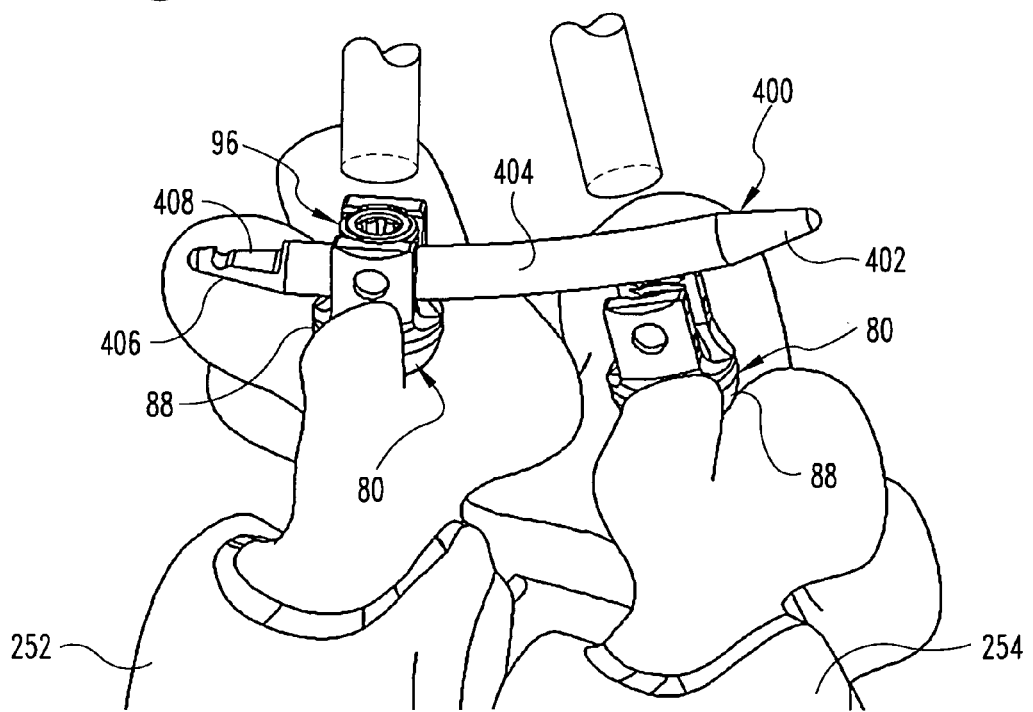
FIG. 59 is the spinal column segment of FIG. 58 with the connecting element engaged to one of the anchors secured to one of the vertebrae.

In either procedure, one end of connecting element 400 is positioned in the passage of the anchor 80 secured to vertebra 252, i.e. the vertebra that is not misaligned, as shown in FIG. 58. The opposite end of connecting element 400 is positioned above the passage of yoke 88 of the anchor 80 secured to vertebra 254. As shown in FIG. 59, a set screw 96 is delivered through or along anchor extension 30 and provisionally tightened to secure connecting element 400 to the anchor 80 secured to vertebra 252. If necessary, anchor extension 100 can be manipulated to contact connecting element 400 and push it toward vertebra 242 change the angle at which connecting element 400 extends from the anchor 80 secured to vertebra 252. Set screw 96 can then be re-tightened to secure connecting element 400 in the adjusted position. This adjustment may be desired to reduce the amount of reduction of vertebra 254 required to position connecting element 400 in the passage of the anchor 80 secured thereto.

Figure 60:
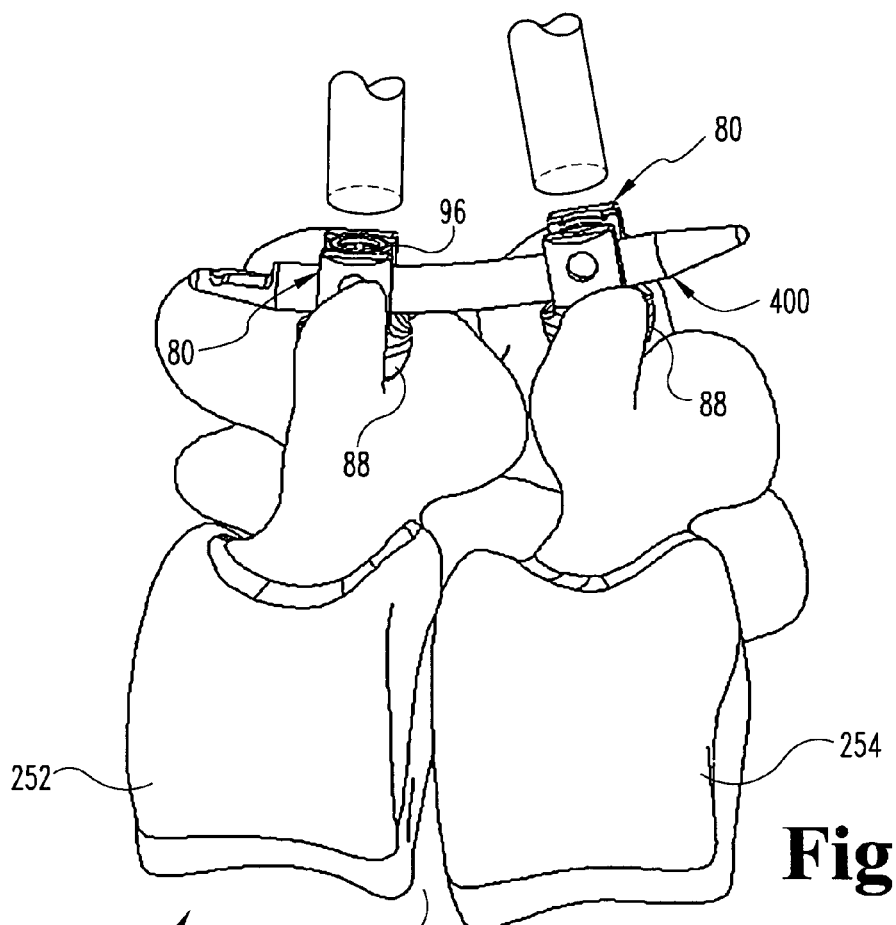
FIG. 60 is the spinal column segment of FIG. 59 with the other anchor and vertebrae reduced into alignment with the vertebrae and anchor to which the connecting element is engaged.
Figure 61:
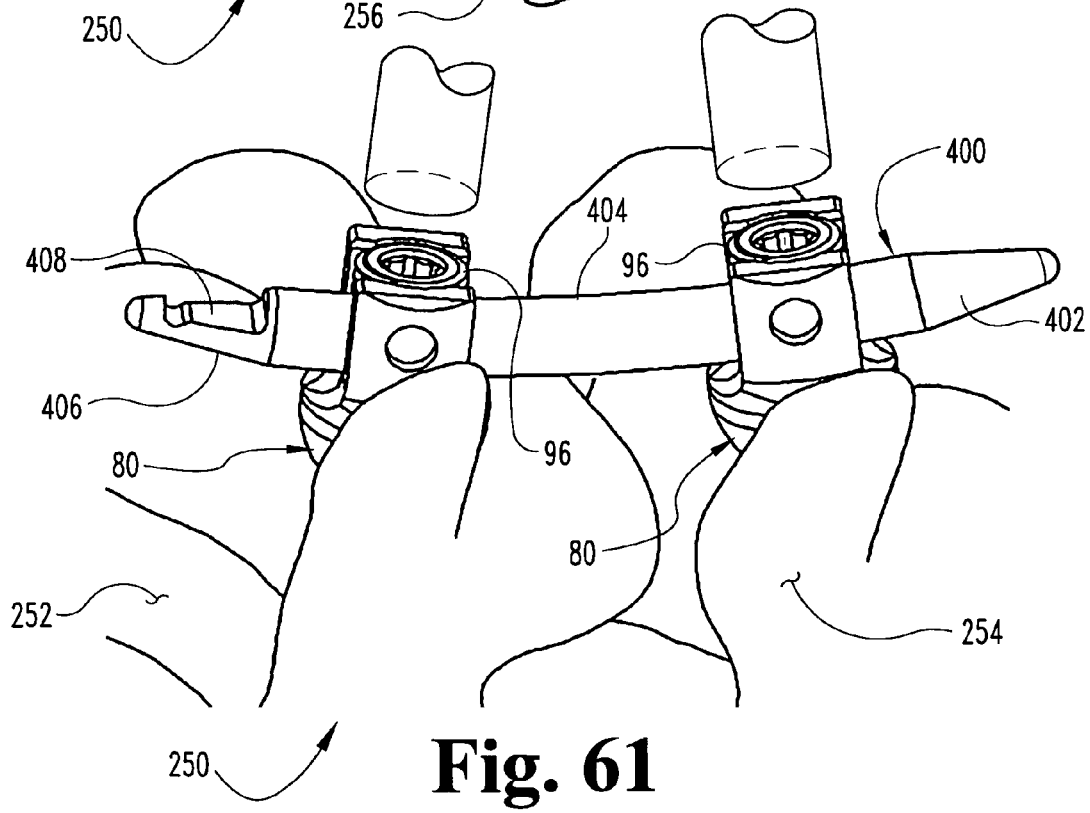
FIG. 61 is the spinal column segment of FIG. 60 with the connecting element engaged to the other anchor.

Anchor extension 100 is then manipulated as discussed above to draw anchor 80 and vertebra 254 into alignment with the vertebra 252 and position connecting element 400 in the passage of yoke 88 of the anchor 80 secured to vertebra 254, as shown in FIG. 60. A set screw 96 is then delivered through anchor extension 100 to secure connecting element 400 to anchor 80 of vertebra 254 as shown in FIG. 61. The set screw 96 of anchor 80 secured to vertebra 252 can be further tightened if necessary. The anchor extensions 30, 100 can then be removed and connecting element 400 maintains vertebrae 252, 254 in align positioned relative to one another.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal stabilization system, comprising:
 an elongate connecting element extending along a longitudinal axis between a rigid first end portion and a rigid second end portion, said connecting element including a flexible intermediate portion extending between and engaged to said first and second end portions;
 first, second and third anchors engageable to respective ones of first, second and third vertebrae when said second vertebra is located between the first and third vertebra, wherein said connecting element is engageable to said first, second and third anchors with said first end portion engageable to said first anchor and said second end portion engageable to at least said third anchor with said intermediate portion positioned between said first anchor and said second anchor; and
 a coupling member extending through said flexible intermediate portion and into said rigid first and second end portions, said coupling member including a first end fixedly engaged to one of said first and second end portions and said coupling member including a second end that is axially movable in the other of said first and second end portions to allow said first and second end portions to move toward one another, said second end of said coupling member including a stop member to limit movement of said first and second end portions away from one another.

2. The system of claim 1, further comprising a second flexible intermediate portion between said second anchor and said third anchor when said second end portion is engaged to said third anchor.

3. The system of claim 2, further comprising a linking portion extending between said flexible intermediate portions and engageable to said second anchor.

4. The system of claim 3, wherein said linking portion is rigid.

5. The system of claim 4, wherein said end portions and said linking portion each include an elongated rod-like body.

6. The system of claim 5, wherein said first end portion includes a flange at an end of said body thereof engaged with one end of said intermediate portion, said linking portion includes flanges at opposite ends of the body thereof engaged to respective ones of said intermediate portions, and said second end portion includes a flange at an end of the body thereof engaged to said second intermediate portion.

7. The system of claim 6, wherein at least one of said flanges includes a plurality of holes therethrough for facilitating engagement of said intermediate portion thereto.

8. The system of claim 1, wherein each of said first and second end portions includes an elongated rod-like body curved along said longitudinal axis.

9. The system of claim 8, wherein said first end portion includes a flange projecting about an end of said body thereof engaged with one end of said intermediate portion, and said second end portion includes a flange projecting about an end of the body thereof engaged to an opposite end of said intermediate portion.

10. The system of claim 9, wherein said flexible intermediate portion includes a cylindrical body comprised of elastomer material.

11. The system of claim 1, wherein said first and second end portions include a first cross-sectional dimension therealong and said flexible intermediate portion includes a second cross-sectional dimension therealong greater than said first cross-sectional dimensions.

12. The system of claim 11, wherein said first and second cross-sections are circular.

13. The system of claim 1, wherein an end member of at least one of said first and second end portions is tapered away from said flexible intermediate portion to facilitate percutaneous introduction of said connecting element to said first, second and third anchors.

14. The system of claim 1, wherein at least one of said first and second end portions includes an indexed configuration at an end thereof opposite said intermediate portion, said indexed configuration for engagement with an insertion instrument with the connecting element in a predetermined orientation relative to the insertion instrument.

15. The system of claim 1, wherein said coupling member is selected from the group consisting of: a cable, a rod, a wire, a tether, a suture and a cord.

16. The system of claim 1, wherein said first end portion includes a first passage, said second end portion includes a second passage, and said intermediate portion includes an intermediate passage aligned with said first and second passages, said coupling member being received in said passages.

17. The system of claim 16, wherein said stop member is received in an enlarged portion of said second passage of said second end portion.

18. The system of claim 17, wherein said stop member is movable along said enlarged portion of said second passage away from said first end portion in response to compression of said flexible intermediate portion.

19. The system of claim 17, wherein said second passage diverges from said longitudinal axis in a direction away from said first end portion and said enlarged portion of said passage opens along a sidewall of said second end portion.

20. The system of claim 17, wherein said second passage extends along the longitudinal axis to an end member of said second end portion located opposite said flexible intermediate portion, said enlarged portion of said second passage opening at said end member.

21. The system of claim 20, wherein said second end portion is curved along said longitudinal axis.

22. A spinal stabilization system, comprising:
a connecting element extending along a longitudinal axis, said connecting element including a first end portion, a linking portion, and a second end portion, said connecting element further comprising a first intermediate portion extending between said first end portion and said linking portion and a second intermediate portion extending between said linking portion and said second end portion, said first end portion, said linking portion and second end portion each being substantially rigid and each being engageable to respective ones of first, second and third anchors engageable to respective ones of first, second and third vertebrae, said intermediate portions being flexible to permit movement of said first and second end portions relative to said linking portion, wherein said connecting element includes a coupling member extending through said first and second intermediate portions, said linking portion, and into said first and second end portions, said coupling member including a first end fixedly engaged to one of said first and second end portions and said coupling member including a second end that is axially movable in the other of said first and second end portions to allow said first and second end portions to move toward one another, said second end of said coupling member including a stop member to limit movement of said first and second end portions away from one another.

23. The system of claim 22, wherein said connecting member is curved along said longitudinal axis.

24. The system of claim 22, wherein said first and second intermediate portions include a cross-sectional area that is greater than a cross-sectional area of said first and second end portions and said linking portion.

25. The system of claim 22, wherein said stop member is abuttable against said second end portion to limit displacement of said first and second end portions away from one another as a result of tensioning of said intermediate portions, said stop member being axially movable along said second end portion in response to compression of said intermediate portions.

26. The system of claim 22, wherein said end portions and said linking portion each include an elongated rod-like body.

27. The system of claim 26, wherein said first end portion includes a flange about an end of said body thereof engaged with one end of said intermediate portion, said linking portion includes flanges about opposite ends of the body thereof engaged to respective ones of the intermediate portions, and said second end portion includes a flange about an end of the body thereof engaged to said second intermediate portion.

28. The system of claim 22, wherein an end member of one of said first and second end portions is tapered away from said flexible intermediate portion to facilitate percutaneous introduction of said connecting element to said first, second and third anchors.

* * * * *